United States Patent
Genta et al.

(10) Patent No.: US 9,982,283 B2
(45) Date of Patent: *May 29, 2018

(54) SACCHARIDE SOLUTION PRODUCTION SYSTEM, SACCHARIDE SOLUTION PRODUCTION METHOD USING BIOMASS RAW MATERIAL, AND ALCOHOL PRODUCTION METHOD USING BIOMASS RAW MATERIAL

(75) Inventors: Minoru Genta, Kobe (JP); Seiichi Terakura, Kobe (JP); Ryosuke Uehara, Kobe (JP); Seiji Kobayashi, Kobe (JP)

(73) Assignee: MITSUBISHI HITACHI POWER SYSTEMS ENVIRONMENTAL SOLUTIONS, LTD., Kanagawa (JP)

( * ) Notice: Subject to any disclaimer, the term of this patent is extended or adjusted under 35 U.S.C. 154(b) by 15 days.

This patent is subject to a terminal disclaimer.

(21) Appl. No.: 14/411,473

(22) PCT Filed: Jul. 11, 2012

(86) PCT No.: PCT/JP2012/067726
§ 371 (c)(1),
(2), (4) Date: Dec. 26, 2014

(87) PCT Pub. No.: WO2014/010048
PCT Pub. Date: Jan. 16, 2014

(65) Prior Publication Data
US 2015/0211038 A1    Jul. 30, 2015

(51) Int. Cl.
| | |
|---|---|
| C12P 19/14 | (2006.01) |
| C13K 1/02 | (2006.01) |
| C12P 7/10 | (2006.01) |
| C13B 20/16 | (2011.01) |
| C12M 1/40 | (2006.01) |
| C12M 1/00 | (2006.01) |
| C12M 1/26 | (2006.01) |
| C12P 7/02 | (2006.01) |
| C12P 19/02 | (2006.01) |

(52) U.S. Cl.
CPC ............ *C12P 19/14* (2013.01); *C12M 21/18* (2013.01); *C12M 29/00* (2013.01); *C12M 29/14* (2013.01); *C12M 33/00* (2013.01); *C12M 45/06* (2013.01); *C12M 45/09* (2013.01); *C12M 45/20* (2013.01); *C12M 47/10* (2013.01); *C12P 7/02* (2013.01); *C12P 7/10* (2013.01); *C12P 19/02* (2013.01); *C13B 20/165* (2013.01); *C13K 1/02* (2013.01); *B01J 2219/0004* (2013.01); *B01J 2219/00006* (2013.01); *C12P 2201/00* (2013.01); *C12P 2203/00* (2013.01); *Y02E 50/16* (2013.01)

(58) Field of Classification Search
None
See application file for complete search history.

(56) References Cited

U.S. PATENT DOCUMENTS

| | | |
|---|---|---|
| 5,348,871 A | 9/1994 | Scott et al. |
| 8,163,517 B2 | 4/2012 | Genta et al. |
| 8,334,113 B2 | 12/2012 | Genta et al. |
| 8,980,060 B2 | 3/2015 | Ishida et al. |
| 9,102,956 B2 | 8/2015 | Genta et al. |
| 9,102,965 B2 | 8/2015 | Genta et al. |
| 9,238,827 B2 | 1/2016 | Genta et al. |
| 9,315,840 B2 | 4/2016 | Genta et al. |
| 9,404,135 B2 | 8/2016 | Genta et al. |
| 9,422,519 B2 | 8/2016 | Suzuki et al. |
| 9,434,971 B2 | 9/2016 | Genta et al. |
| 9,567,558 B2 | 2/2017 | Suzuki et al. |
| 2008/0044891 A1 | 2/2008 | Kinley et al. |
| 2010/0184176 A1* | 7/2010 | Ishida ............... B01D 11/0226 435/165 |
| 2010/0285574 A1* | 11/2010 | Genta ............... B01D 11/0226 435/289.1 |
| 2011/0003348 A1 | 1/2011 | Genta et al. |
| 2011/0008826 A1 | 1/2011 | Hanakawa et al. |

(Continued)

FOREIGN PATENT DOCUMENTS

| | | |
|---|---|---|
| AU | 2009222310 A1 | 9/2009 |
| CA | 2654306 A1 | 8/2009 |

(Continued)

OTHER PUBLICATIONS

Notice of Acceptance in AU Application No. 2012385156, dated Apr. 6, 2016.
Office Action dated Aug. 18, 2015, corresponding to Japanese patent application No. 2014-524541.
Decision of a Patent Grant in JP Application No. 2014-524541, dated Mar. 1, 2016.
Notice of Allowance in CA Application in 2,876,108, dated Aug. 3, 2016.

(Continued)

*Primary Examiner* — Suzanne M Noakes
*Assistant Examiner* — Stephen M Chong
(74) *Attorney, Agent, or Firm* — Hauptman Ham, LLP

(57) ABSTRACT

Provided is a biomass hydrothermal decomposition system which includes: a biomass supply unit that supplies a biomass raw material; hydrothermally decomposing the biomass raw material using pressurized hot water; a hydrothermal decomposition unit that dissolves lignin components and hemicellulose components in the pressurized hot water; a biomass solid fraction discharge unit that discharges a biomass solid fraction from the hydrothermal decomposition unit; an enzymatic liquefaction tank that is in connection with the biomass solid fraction discharge unit, and in which the discharged biomass solid fraction is introduced, and an enzyme is supplied to the biomass solid fraction to liquefy the biomass solid fraction; and a discharge unit that discharges the liquefied biomass solid fraction.

8 Claims, 14 Drawing Sheets

(56) References Cited

U.S. PATENT DOCUMENTS

| | | |
|---|---|---|
| 2011/0300617 A1 | 12/2011 | Genta et al. |
| 2012/0009626 A1 | 1/2012 | Suzuki et al. |
| 2012/0009642 A1 | 1/2012 | Suzuki et al. |
| 2012/0058544 A1 | 3/2012 | Genta et al. |
| 2013/0078697 A1 | 3/2013 | Ukai et al. |
| 2013/0122555 A1 | 5/2013 | Suzuki et al. |
| 2013/0273608 A1 | 10/2013 | Hanakawa et al. |

FOREIGN PATENT DOCUMENTS

| | | |
|---|---|---|
| CA | 2717298 A1 | 9/2009 |
| CA | 2666152 A1 | 4/2010 |
| CA | 2750754 A1 | 1/2012 |
| CA | 2744522 A1 | 3/2012 |
| CN | 101960016 A | 1/2011 |
| EP | 2251427 A1 | 11/2010 |
| JP | 09-507386 A | 7/1997 |
| JP | 11-506934 A | 6/1999 |
| JP | 2002-59118 A | 2/2002 |
| JP | 2005-27541 A | 2/2005 |
| JP | 2005-168335 A | 6/2005 |
| JP | 2005-229821 A | 9/2005 |
| JP | 2009-183154 A | 8/2009 |
| JP | 2009-183805 A | 8/2009 |
| JP | 4764527 B1 | 9/2011 |
| JP | 4875785 B1 | 2/2012 |
| JP | 5077346 B2 | 11/2012 |
| KR | 10-2010-0127746 A | 12/2010 |
| WO | 2009/096062 A1 | 8/2009 |
| WO | 2009/110374 A1 | 9/2009 |
| WO | 2012/004894 A1 | 1/2012 |
| WO | 2012/004895 A1 | 1/2012 |
| WO | 2012/029182 A1 | 3/2012 |

OTHER PUBLICATIONS

Gregg et al., "Bioconversion of Lignocellulosic Residue to Ethanol: Process Flowsheet Development", Biomass and Bioenergy, vol. 9, Nos. 1-5, pp. 287-302, 1995, Elsevier Science Ltd, Great Britain.
International Search Report received in corresponding International Application No. PCT/JP2012/067726, dated Sep. 25, 2012.
Office Action in U.S. Appl. No. 13/700,753, dated Sep. 21, 2017. 11pp.
English Translation of written opinion of the international searching authority dated Sep. 25, 2012 corresponding to PCT/JP2012/067726.

* cited by examiner

FIG.13
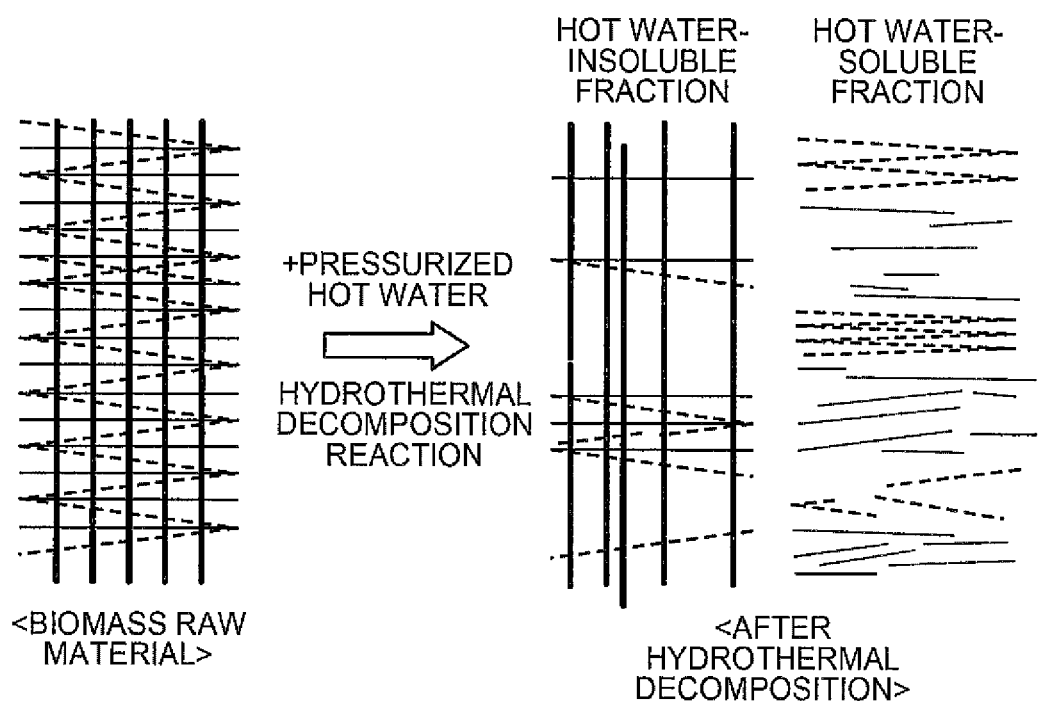
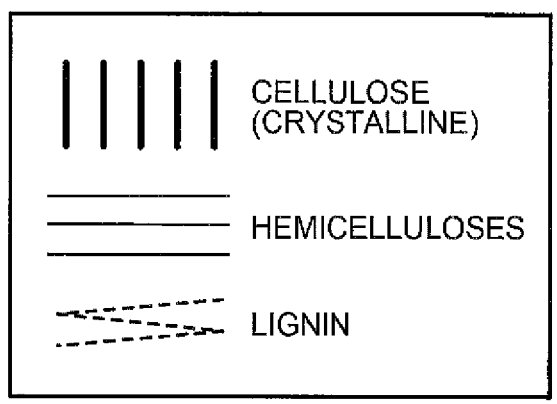

SACCHARIDE SOLUTION PRODUCTION SYSTEM, SACCHARIDE SOLUTION PRODUCTION METHOD USING BIOMASS RAW MATERIAL, AND ALCOHOL PRODUCTION METHOD USING BIOMASS RAW MATERIAL

RELATED APPLICATIONS

The present application is a National Phase of International Application Number PCT/JP2012/067726, filed Jul. 11, 2012.

FIELD

The present invention relates to a biomass hydrothermal decomposition system that enables efficient decomposition of a biomass raw material, a method for producing a saccharide solution using a biomass raw material, and a method for producing an alcohol using a biomass raw material.

BACKGROUND

Technologies for producing ethanol and the like by saccharifying woody biomass or other biomass using dilute sulfuric acid or concentrated sulfuric acid, subsequently subjecting the resultant saccharides to solid-liquid separation, neutralizing the liquid phase, and utilizing the resultant components as raw materials for ethanol fermentation or the like, have been hitherto put to practical use (Patent Literature 1 and Patent Literature 2).

Furthermore, production of industrial chemical raw materials (for example, lactic acid fermentation) using saccharides as staring raw materials have been also considered.

The term biomass as used herein refers to a living organism, or accumulation of organic materials derived from living organisms, that has been incorporated into the material circulation system of the global biosphere (see JIS K 3600 1258).

Here, sugarcane, corn and the like that are currently used as alcohol raw materials have been originally used for food. However, using these food resources stably as long-term industrially utilized resources is not preferable from the viewpoint of the life cycle of valuable foods.

For this reason, it is an important challenge to efficiently utilize cellulosic resources such as herbaceous biomass and woody biomass, which are considered as potentially useful resources.

Furthermore, cellulosic resources have compositions varying from 38% to 50% of cellulose and from 23% to 32% of hemicellulose components, and also include lignin components, which are not used as fermentation raw materials, at a proportion varying from 15% to 22%. Due to the research on industrialization with many problems still remaining unsolved, raw materials are assumed to be fixed, and under the current situation, no technologies have been disclosed on production systems that take into consideration of the diversity of raw materials.

Furthermore, since it is contemplated to aim at providing countermeasures against garbage problems, global warming and the like with raw materials which are more disadvantageous as fermentation raw materials than starch raw materials, production systems involving fixed raw materials have almost no meaning. A production system is useless if it is not applicable to a wide variety of general waste materials. It is the current situation that enzymatic saccharification methods are also considered to be poorly efficient per se and pose problems to be solved in the future. The saccharification ratio obtainable by acid treatment also has a small value of approximately 75% (on the basis of components that can be saccharified), due to excessive decomposition of saccharides caused by excessive reaction, and the like. Therefore, the ethanol production yield remains only at approximately 25% based on cellulosic resources (Patent Literature 3).

In the prior art technologies of Patent Literatures 1 to 3, there has been a phenomenon in which side reaction products cause inhibition of enzymatic saccharification, and the saccharide yield is decreased. Therefore, hydrothermal decomposition apparatuses that eliminate enzymatic saccharification inhibiting materials and increase the enzymatic saccharifiability of cellulose main constituent, have been previously suggested (Patent Literatures 4 to 7).

CITATION LIST

Patent Literature

Patent Literature 1: JP 9-507386 W
Patent Literature 2: JP 11-506934 W
Patent Literature 3: JP 2005-168335 A
Patent Literature 4: JP 2009-183805 A
Patent Literature 5: JP 2009-183154 A
Patent Literature 6: JP 4764527 B1

SUMMARY

Technical Problem

In regard to the suggestion of the hydrothermal decomposition apparatus according to Patent Literature 6 described above, when a slurry is produced in an enzymatic liquefaction vessel, since water is supplied from the outside, there is a problem that a large amount of water is used in the plant as a whole, and economic efficiency of the plant is deteriorated.

The present invention was achieved in view of the problems described above, and an object of the present invention is to provide a biomass hydrothermal decomposition system with enhanced plant efficiency, a method for producing a saccharide solution using a biomass raw material, and a method for producing an alcohol using a biomass raw material.

Solution to Problem

According to a first aspect of the present invention in order to solve the above-problems, there is provided a biomass hydrothermal decomposition system including: a biomass supply unit that supplies a biomass raw material containing cellulose, hemicelluloses, and lignin at a pressure ranging from normal pressure to an added pressure; a hydrothermal decomposition unit that hydrothermally decomposes the biomass raw material by pressurized hot water, and dissolves lignin components and hemicellulose components in the pressurized hot water; a biomass solid fraction discharge unit that discharges a biomass solid fraction from the hydrothermal decomposition unit; and an enzymatic liquefaction tank that is in connection with the biomass solid fraction discharge unit, and in which the discharged biomass solid fraction is introduced, and at the same time, an enzyme is supplied to the biomass solid fraction to liquefy the biomass solid fraction.

According to a second aspect of the present invention, there is provided the biomass hydrothermal decomposition system according to the first aspect, wherein the hydrothermal decomposition unit conveys the biomass raw material that has been supplied from the side of an end of the apparatus main body to the side of the other end of the apparatus main body by a conveyance means inside the apparatus main body, supplies pressurized hot water from the side of an end different from the supply site of the biomass raw material to the inside of the apparatus main body, hydrothermally decomposes the biomass raw material by bringing the biomass raw material and the pressurized hot water into countercurrent contact, transfers hot water-soluble components in a hot water discharge liquid, which is pressurized hot water to be discharged, and separates lignin components and hemicellulose components from the biomass raw material.

According to a third aspect of the present invention, there is provided the biomass hydrothermal decomposition system according to the first or second aspect, further including a first saccharification tank that saccharifies the biomass solid fraction that has been liquefied in the enzymatic liquefaction tank.

According to a fourth aspect of the present invention, there is provided the biomass hydrothermal decomposition system according to any one of the first to third aspects, further including a second saccharification tank that saccharifies a hot water discharge liquid produced from the hydrothermal decomposition unit.

According to a fifth aspect of the present invention, there is provided the biomass hydrothermal decomposition system according to the third aspect, further including: a first solid-liquid separation apparatus that separates a solid fraction from the saccharide solution obtained after saccharification in the first saccharification tank; and a first water separation apparatus that removes water from the saccharide solution obtained after solid separation.

According to a sixth aspect of the present invention, there is provided the biomass hydrothermal decomposition system according to the fourth aspect, further including: a second solid-liquid separation apparatus that separates a solid fraction from the saccharide solution obtained after saccharification in the second saccharification tank; and a second water separation apparatus that removes water from the saccharide solution obtained after solid separation.

According to a seventh aspect of the present invention, there is provided the biomass hydrothermal decomposition system according to the first aspect, wherein the system further comprises a hot water discharge liquid inlet line that introduces a hot water discharge liquid including a biomass hot water-soluble fraction, which is discharged from the hydrothermal decomposition unit, to the enzymatic liquefaction tank, and the liquefied biomass solid fraction is mixed with a hot water discharge liquid to obtain a mixed liquefaction product.

According to an eighth aspect of the present invention, there is provided the biomass hydrothermal decomposition system according to the seventh aspect, wherein a filter is interposed in the hot water discharge liquid inlet line.

According to a ninth aspect of the present invention, there is provided the biomass hydrothermal decomposition system according to the seventh aspect, wherein a cooling means is interposed in the discharge liquid inlet line.

According to a tenth aspect of the present invention, there is provided the biomass hydrothermal decomposition system according to the seventh aspect, further including a saccharification tank that performs saccharification using a mixed liquefaction product liquefied in the enzymatic saccharification tank.

According to an eleventh aspect of the present invention, there is provided a biomass hydrothermal decomposition system according to the tenth aspect, further including: a solid-liquid separation apparatus that separates a solid fraction from the saccharide solution obtained after saccharification in the saccharification tank; and a water separation apparatus that removes water from the saccharide solution obtained after solid separation.

According to a twelfth aspect of the present invention, there is provided a method for producing a saccharide solution using a biomass raw material, the method including: supplying a biomass raw material containing cellulose, hemicelluloses and lignin at a pressure ranging from normal pressure to an added pressure, hydrothermally decomposing the biomass raw material by a hydrothermal decomposition unit using pressurized hot water, dissolving lignin components and hemicellulose components in the pressurized hot water, subsequently introducing an enzyme to a biomass solid fraction discharged from the hydrothermal decomposition unit, liquefying the biomass solid fraction in an enzymatic liquefaction tank that is in connection with the hydrothermal decomposition unit, subsequently subjecting the liquefied biomass solid fraction to monosaccharification by an enzyme, and producing a saccharide solution of monosaccharides.

According to a thirteenth aspect of the present invention, there is provided the method for producing a saccharide solution using a biomass raw material according to the twelfth aspect, wherein enzymatic liquefaction of the biomass solid fraction is carried out under pressurized conditions, and the liquefied biomass solid fraction is discharged and is subjected to enzymatic monosaccharification under normal pressure conditions.

According to a fourteenth aspect of the present invention, there is provided the method for producing a saccharide solution using a biomass raw material according to the twelfth aspect, wherein a mixed liquefaction product is obtained, while a hot water discharge liquid including a biomass hot water-soluble fraction discharged from the hydrothermal decomposition unit is introduced into the enzymatic liquefaction tank.

According to a fifteenth aspect of the present invention, there is provided the method for producing a saccharide solution using a biomass raw material according to the fourteenth aspect, wherein production of the saccharide solution of monosaccharides is carried out by performing enzymatic saccharification under normal pressure conditions.

According to a sixteenth aspect of the present invention, there is provided a method for producing an alcohol, the method including performing alcohol fermentation using the saccharide solution obtained by the method for producing a saccharide solution using a biomass raw material according to any one of the twelfth to fifteenth aspects, and thereby producing an alcohol.

Advantageous Effects of Invention

According to the present invention, an enzyme is supplied, in a hydrothermal decomposition unit, to a biomass solid fraction obtained by dissolving lignin components and hemicellulose components in pressurized hot water, the biomass solid fraction is liquefied, and the liquefied material becomes a liquid seal, so that effluence of the pressurizing gas in the hydrothermal decomposition unit can be prevented.

Furthermore, since it is not necessary to form slurry by supplying water from the outside, the amount of water introduced when a slurrying treatment is conducted is reduced, and an enhancement of the plant efficiency can be promoted.

BRIEF DESCRIPTION OF DRAWINGS

FIG. 13 is a diagram illustrating the state of decomposition of biomass by hot water.

DESCRIPTION OF EMBODIMENTS

Hereinafter, this invention will be described in detail with reference to the drawings. Meanwhile, this invention is not intended to be limited by these embodiments. Also, the constituent elements in the embodiments described below include elements that are easily conceived by a person ordinarily skilled in the art, or elements that are substantially equivalent thereto.

First Embodiment

The biomass hydrothermal decomposition system according to the present invention will be described with reference to the drawings.

Figure 1:
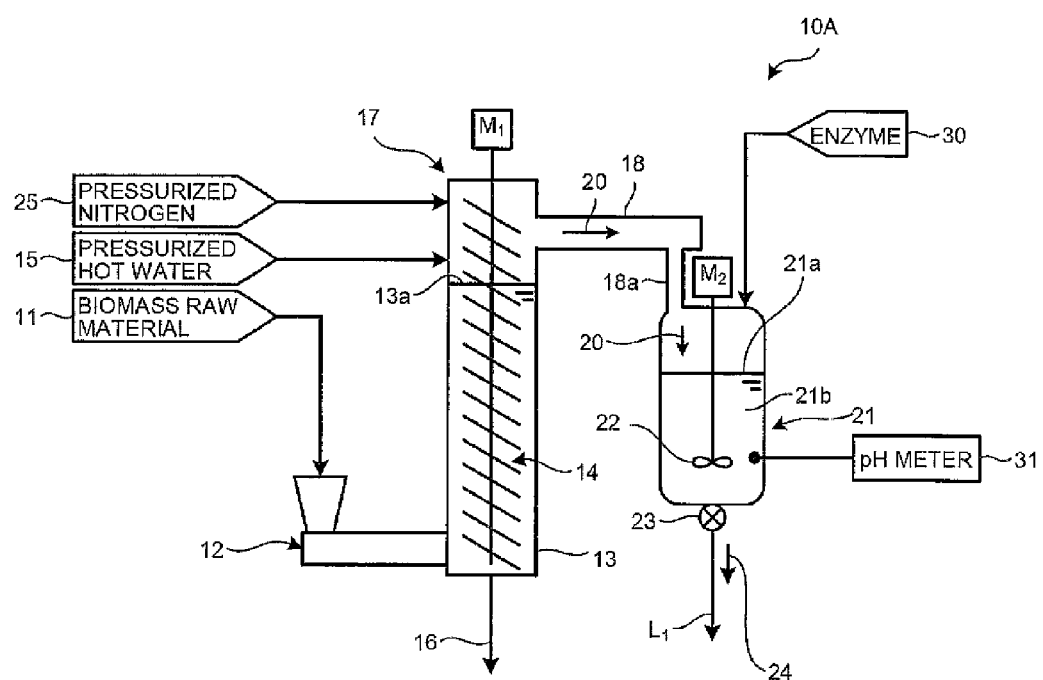
FIG. 1 is an outline diagram of a biomass hydrothermal decomposition system according to a first embodiment.
Figure 2:
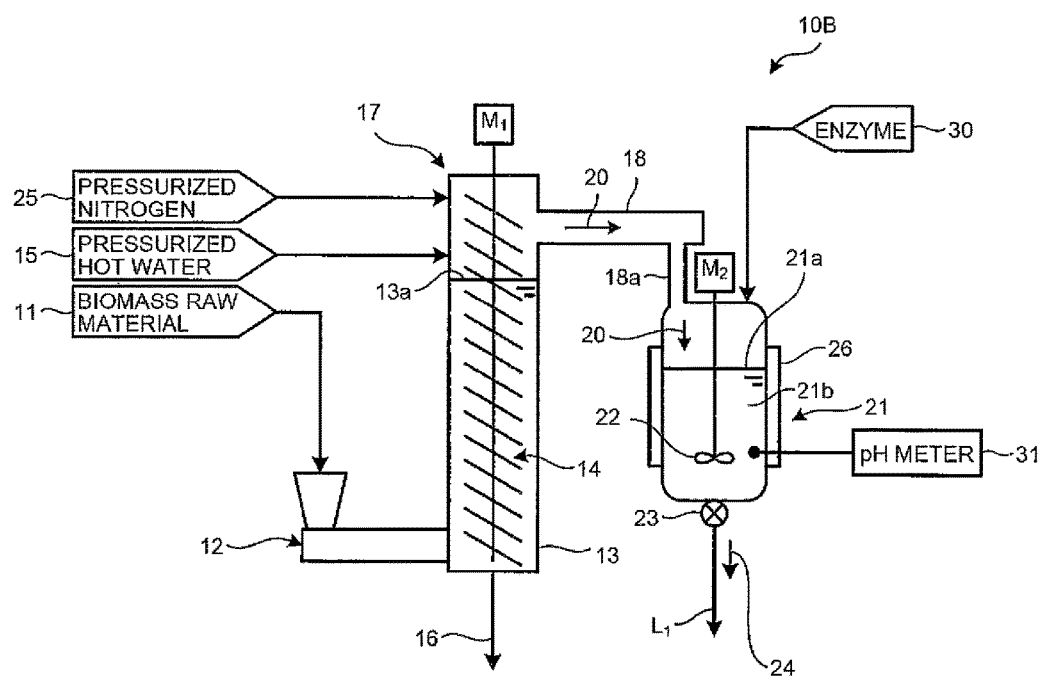
FIG. 2 is an outline diagram of another biomass hydrothermal decomposition system according to the first embodiment.
Figure 3:
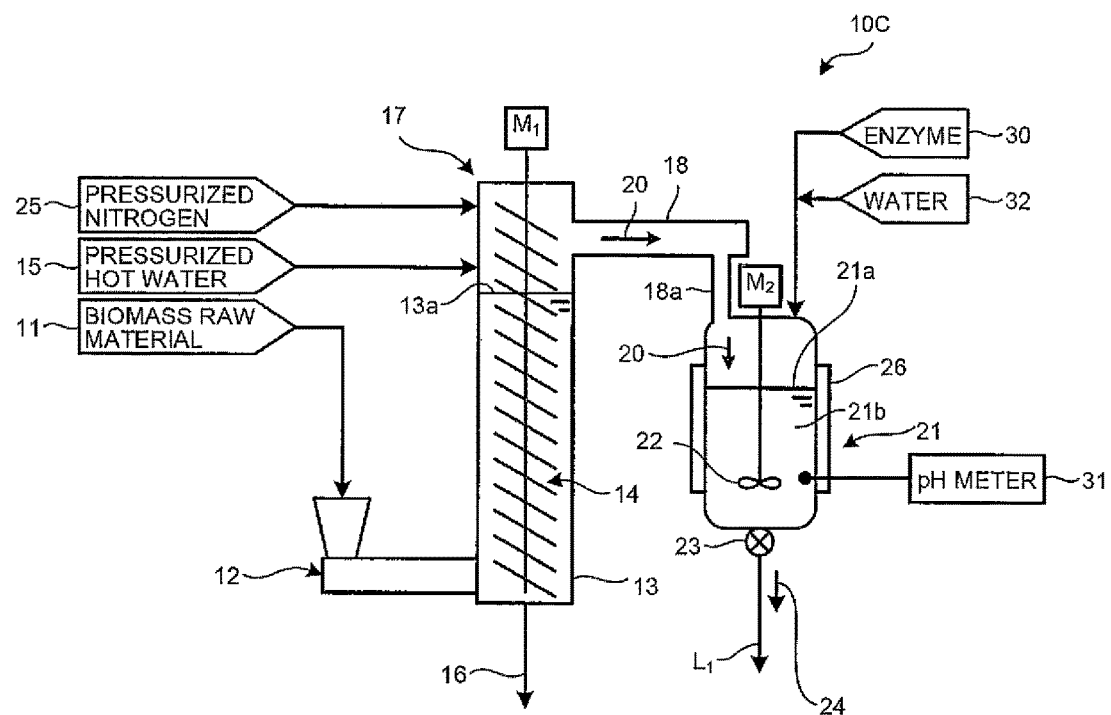
FIG. 3 is an outline diagram of another biomass hydrothermal decomposition system according to the first embodiment.

FIG. 1 is an outline diagram of a biomass hydrothermal decomposition system related to the first embodiment. FIGS. 2 and 3 are outline diagrams of other biomass hydrothermal decomposition systems related to the first embodiment.

First, as illustrated in FIG. 1, a biomass hydrothermal decomposition system 10A according to the present embodiment includes: a biomass supply unit 12 that supplies a biomass raw material 11 containing cellulose, hemicelluloses and lignin at a pressure ranging from normal pressure to an elevated pressure; a hydrothermal decomposition unit 17 that hydrothermally decomposes the biomass raw material 11 using pressurized hot water (hereinafter, also referred to as "hot water") 15, and dissolving lignin components and hemicellulose components in the pressurized hot water 15; a biomass solid fraction discharge unit 18 that discharges a biomass solid fraction 20 from the hydrothermal decomposition unit 17; an enzymatic liquefaction tank 21 that is in connection with the biomass solid fraction discharge unit 18, and to which the discharged biomass solid fraction 20 is fed, and at the same time, an enzyme 30 is supplied to the biomass solid fraction 20 to liquefy the biomass solid fraction 20; and a discharge unit 23 that discharges the liquefied biomass solid fraction 24 at a pressure ranging from an elevated pressure to normal pressure.

Regarding the hydrothermal decomposition unit 17, a known hydrothermal treatment apparatus that decomposes the biomass raw material 11 under high temperature and high pressure conditions can be used. An example of the hydrothermal decomposition system will be explained using FIG. 1, but the present invention is not intended to be limited to this hydrothermal decomposition system.

As illustrated in FIG. 1, in the hydrothermal decomposition system related to the present embodiment, the biomass raw material 11 supplied to the hydrothermal decomposition unit 17 is conveyed from the lower part to the upper part inside an apparatus main body 13 by a first screw means 14, which is a conveyance means, and also, the pressurized hot water 15 is supplied from a side in the upper part different from the supply site for the biomass raw material 11, to the inside of the apparatus main body 13. Thus, the biomass raw material 11 is hydrothermally decomposed while the pressurized hot water 15 is brought into countercurrent contact with the raw material, and hot water-soluble components (lignin components and hemicellulose components) are transferred into a hot water discharge liquid 16, which is pressurized hot water to be discharged. Thus, lignin components and hemicellulose components are separated from the biomass raw material 11 in the hydrothermal decomposition system.

Here, regarding the conveyance means, a screw means is taken as an example in the present embodiment. However, it is not limited to the screw means as long as it is capable of conveying the biomass solid fraction 20 from the lower part to the upper part, and for example, a method of slowly extruding the biomass solid fraction by compaction filling may be used.

Furthermore, in the present embodiment, the biomass solid fraction 20 is conveyed by a conveyance means from the lower side of one end of the apparatus to the upper side of the other end, and also, hot water is supplied from the upper side of the other end. However, the present invention is not limited to this, and it is also acceptable to supply the biomass solid fraction 20 from the upper side and supply hot water from the lower side so as to bring the components into countercurrent contact.

In the present embodiment, the discharged biomass solid fraction 20 is partially liquefied by the enzyme 30 that has been fed into the enzymatic liquefaction tank 21, and a liquid surface is formed. Therefore, liquid sealing intended for preventing the leakage of pressurized nitrogen 25 for pressurization is enabled.

Furthermore, in order to carry out the enzymatic reaction smoothly, as can be seen from a biomass hydrothermal decomposition system 10B related to the embodiment illustrated in FIG. 2, the enzymatic liquefaction tank 21 may be provided with a cooling means 26. Meanwhile, in the case of using an enzyme that is resistant to high temperature, the cooling means may be unnecessary. Regarding the cooling means 26, the interior of the enzymatic liquefaction tank 21 may be cooled to a temperature at which the enzyme exhibits its performance, on any one or both of the external side and the internal side of the enzymatic liquefaction tank 21.

Also, when cooling is performed with the cooling means 26, excessive decomposition of hemicelluloses (decomposition initiation temperature: about 140° C. to 180° C.) contained in the water included in the biomass solid fraction 20 can be suppressed.

For this reason, as can be seen from a biomass hydrothermal decomposition system 10C related to the embodiment illustrated in FIG. 3, water 32 may be separately supplied to the enzymatic liquefaction tank 21 to cool the interior thereof, and to also adjust the water content in the liquefied biomass solid fraction 24. In this case, regarding the water 32 to be supplied, for example, water that is conventionally used in the range of 0° C. to 60° C. (for example, pure water, industrial water, or water that has been obtained by cooling pure water, industrial water or the like utilizing cooling tower water, chiller water or the like), and the like can be used. Furthermore, the water separated from the system can also be recycled and reused.

Here, in FIG. 1, reference numeral 18a represents a passage that communicates the biomass solid fraction discharge unit 18 with the enzymatic liquefaction tank 21; 22 represents a stirring means that stirs the interior of the enzymatic liquefaction tank 21; 13a represents the gas-liquid interface of the hydrothermal decomposition unit 17; 21a represents the gas-liquid interface of the enzymatic liquefaction tank 21; $L_1$ represents a discharge line; $M_1$ represents a motor that drives the first screw means 14; and $M_2$ represents a motor that drives the stirring means 22.

Figure 12:
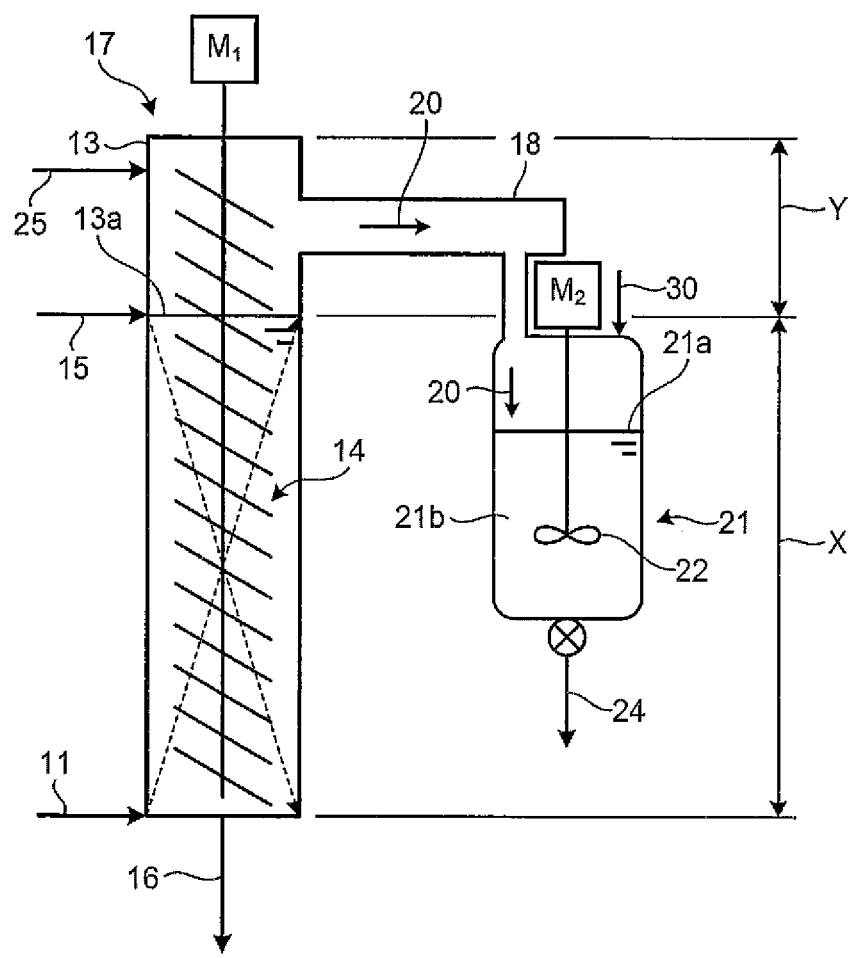
FIG. 12 is a schematic diagram of a vertical type hydrothermal decomposition apparatus that hydrothermally decomposes biomass with hot water.

Next, an outline of the hydrothermal decomposition of the biomass raw material 11 by the hydrothermal decomposition unit 17 will be explained. FIG. 12 is a schematic diagram of a vertical type hydrothermal decomposition apparatus that hydrothermally decomposes biomass with hot water, and FIG. 13 is a diagram illustrating the state of decomposition of biomass by hot water.

In the hydrothermal decomposition unit 17, the biomass raw material 11 and pressurized hot water 15 are supplied to be brought into countercurrent contact, and are thereby subjected to a hydrothermal reaction by internal heat exchange. FIG. 12 shows a countercurrent contact region X and a non-countercurrent contact region Y, and the non-countercurrent contact region Y is in a high temperature high pressure state. Thus, even in the non-countercurrent contact region Y, the hydrothermal decomposition reaction of the biomass solid fraction 20 proceeds, and occasionally, excessive decomposition occurs.

As illustrated in FIG. 12, in the vertical type hydrothermal decomposition apparatus, the biomass raw material (solid) 11 is supplied to the inside of the apparatus main body 13 from the lower side, and is transported to the upper side by the first screw means 14 provided inside the apparatus main body 13. The biomass solid fraction (hot water-insoluble fraction) 20 is dropped from the upper side through the biomass solid fraction discharge unit 18 into a liquid 21b in the enzymatic liquefaction tank 21, which is formed when the enzyme 30 is supplied.

As illustrated in FIG. 13, the biomass (cellulosic raw material) raw material 11 includes hemicelluloses and lignin in addition to cellulose. Specifically, the biomass raw material 11 has a structure in which cellulose is bundled by hemicellulose, and lignin is adhered thereto.

After hydrothermal decomposition, the biomass can be divided into a hot water-insoluble fraction (solid fraction) and a hot water-soluble fraction. The hot water-insoluble fraction (biomass solid fraction 20) is mainly composed of cellulose (raw material of C6 saccharides), and the hot water-soluble fraction (hot water discharge liquid 16) is mainly composed of hemicelluloses (raw material of C5 saccharides). Saccharides can be obtained by saccharifying the respective fractions by means of enzymes.

Therefore, the biomass raw material 11 is hydrothermally decomposed by pressurized hot water 15 in a temperature range of high temperatures (180° C. to 240° C.), and hemicelluloses are decomposed and dissolved in the hot water side, while lignin is also decomposed and dissolved at the same time. As a result, hemicelluloses and the like are dissolved in the hot water side.

In the state of hot water-solubilized hemicelluloses after being solubilized by hot water, excessive decomposition occurs in a temperature range of 140° C. or higher.

This excessive decomposition of hemicelluloses causes a decrease in the yield of hemicelluloses that become a raw material of C5 saccharides. Therefore, it is necessary to suppress excessive decomposition of the hemicelluloses of the hot water-soluble fraction.

Furthermore, since incorporation of excessive decomposition products into hot water is causative of reaction inhibition in the saccharification process by an enzyme and the fermentation process such as alcohol fermentation in the downstream side facilities, it is also necessary to inhibit the generation of this inhibiting substances.

In FIG. 1, the biomass solid fraction discharge unit 18 is provided with a second screw means that is not depicted in the diagram, and the second screw means slowly discharges the biomass solid fraction 20, which constitutes the hot water-insoluble fraction that has been conveyed from the lower part to the upper part by the first screw means 14, toward the enzymatic liquefaction tank 21. Then, the discharged biomass solid fraction 20 is sequentially dropped from the passage 18a into the liquid 21b, and liquefaction is accelerated by stirring of the stirring means 22 provided inside the enzymatic liquefaction tank 21.

Figure 14:
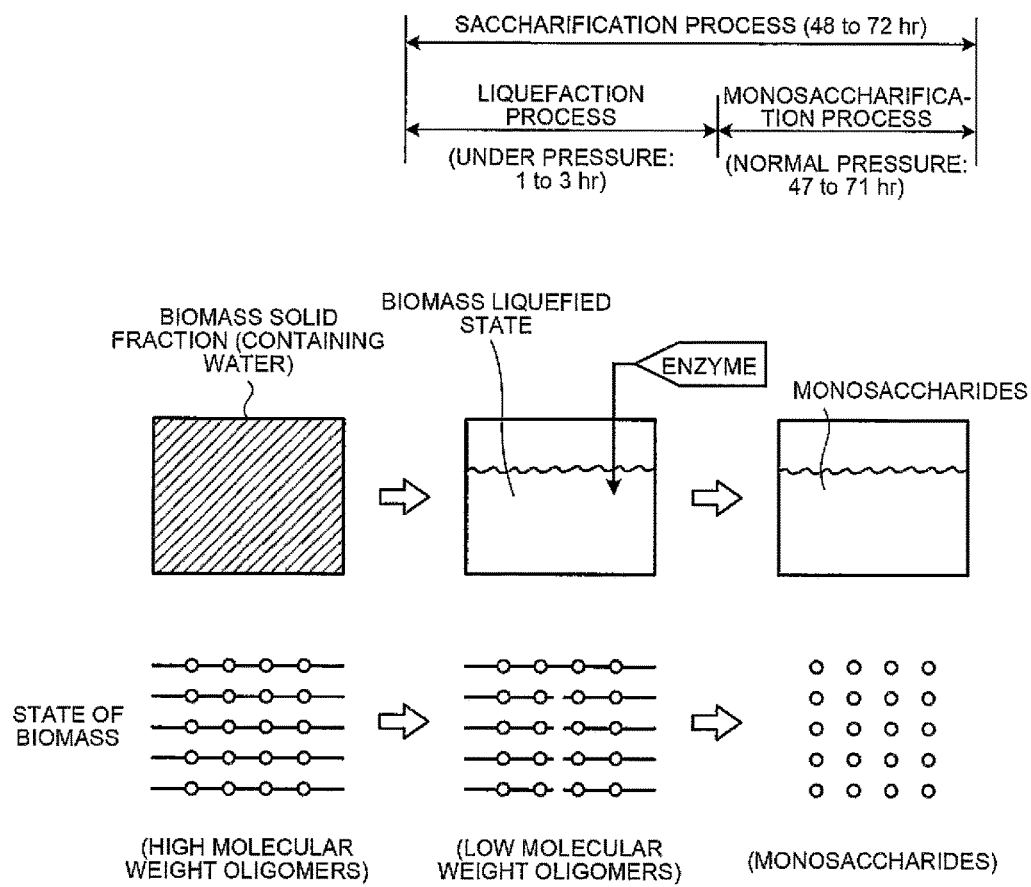
FIG. 14 is a schematic diagram of a saccharification process of liquefaction of a biomass solid fraction by an enzyme and monosaccharification.

FIG. 14 is a schematic diagram of the saccharification process of liquefaction and monosaccharification of the biomass solid fraction by an enzyme. An outline of the saccharification process will be explained based on FIG. 14.

As illustrated in FIG. 14, the biomass solid fraction 20 discharged from the biomass solid fraction discharge unit 18 is in the form of high molecular weight oligomers. These high molecular weight oligomers are sparingly soluble.

When an enzyme is added to these high molecular weight oligomers, a portion of the high molecular weight oligomers is decomposed to low molecular weight oligomers, which are soluble in the water included in the biomass solid fraction 20. The biomass is now in the form of liquefied biomass, and is in a slurry form.

Then, when these low molecular weight oligomers are further subjected to enzymatic saccharification over time, the oligomers become monosaccharides.

Therefore, the saccharification process is a combination of this liquefaction process and a monosaccharification process.

Here, in the present embodiment, since the enzymatic liquefaction tank 21 is under pressurized conditions, a pressure-resistant pressure vessel is used as the tank.

Since this pressure vessel requires production cost, using a large capacity pressure vessel required for saccharification involves cost. Therefore, in the pressure vessel, only the liquefaction process requires pressurized conditions, and the liquefaction process is completed within 1 to 3 hours. After completion of the liquefaction process, the product is discharged under pressurized conditions to normal pressure conditions through a discharge unit 23 provided in the vicinity of the bottom of the enzymatic liquefaction tank 21.

Then, a saccharification treatment is carried out, for example, for 47 to 71 hours using a saccharification tank under normal pressure conditions, and monosaccharification is carried out. Thus, hexoses are obtained from cellulose in the biomass solid fraction 20.

Meanwhile, the time of the saccharification process is only an example, and the time is appropriately set depending on the saccharification conditions (temperature, kind of enzyme, and the like).

Furthermore, when the biomass solid fraction 20 is dropped into the liquid 21b in the enzymatic liquefaction tank 21, the biomass solid fraction 20 is cooled by direct heat exchange with the liquid 21b. As a result, excessive decomposition of residual hemicelluloses, residual lignin, and cellulose as the main component by the hot water included in the biomass solid fraction 20 is suppressed.

In this regard, in the gas atmosphere on the upper side of the gas-liquid interface 13a of the hydrothermal decomposition unit 17, the biomass solid fraction 20 is exposed above the hot water liquid surface (gas-liquid interface 13a) by the first screw means 14. However, since the reaction still proceeds in a high temperature high pressure state due to the presence of the pressurized hot water 15 included in the biomass solid fraction 20, the reaction can be terminated by feeding the biomass solid fraction 20 into the liquid 21b in the enzymatic liquefaction tank 21.

Through this termination of reaction, excessive decomposition of residual hemicelluloses, residual lignin, and cellulose as the main component is suppressed. Thus, excessive decomposition of the cellulose fraction is suppressed, the recovery ratio thereof is enhanced, and also, production of reaction inhibiting components in the downstream side is suppressed.

Furthermore, since the enzyme 30 is supplied into the enzymatic liquefaction tank 21, and the liquid 21b exists as a result of liquefaction by the enzyme, liquid sealing is achieved at the gas-liquid interface 13a of the hydrothermal decomposition unit 17 and at the gas-liquid interface 21a of the enzymatic liquefaction tank 21. Thereby, prevented is the leakage of pressurized nitrogen 25, which is a gas for pressurization (for example, pressurized nitrogen or pressurized air). Thereby, the loss accompanied by gas leakage is lost, and reduction of the running cost applicable to the gas for pressurization can be promoted to a large extent. Meanwhile, the enzymatic liquefaction tank 21 is provided with a safety valve or an inflow passage for the pressurized nitrogen 25, both of which are not shown in the diagram.

Furthermore, fluidization is enabled by enzymatically liquefying the biomass solid fraction 20 and thereby converting a portion thereof to low molecular weight oligomers. Thus, the discharge mechanism at the time of discharging the biomass solid fraction 20 from the enzymatic liquefaction tank 21 to the outside is simplified. That is, if the biomass solid fraction 20 is in a high temperature state, it is necessary to use, for example, highly expensive materials for the materials of the discharge mechanism. However, since the biomass solid fraction is cooled in the enzymatic liquefaction tank 21, inexpensive stainless steel, a resin or the like can be used for the material of the discharge unit 23 that is provided in the discharge side. Regarding this discharge unit 23, for example, a rotary feeder or a flow rate adjusting valve can be used.

Furthermore, since the biomass solid fraction 20 has a high porosity and a small bulk density, handleability thereof while being solid has been complicated. However, enzymatic liquefaction now enables promotion of volume reduction, and handleability is facilitated.

That is, before being added to the liquid 21b, the biomass solid fraction 20 is in a so-called cake state or sponge state, with a high proportion occupied by a gas for pressurization, a high porosity, and a small bulk density such as 0.5 g/cc or less. When this is enzymatically liquefied, the porosity is decreased, and volume reduction is promoted.

Moreover, as the biomass solid fraction 20 is enzymatically liquefied to be slurry, fluidization is enabled, and handling in the subsequent processes is made easier.

Furthermore, when slurrying for fluidity enhancement was carried out in the past, it was necessary to introduce a large amount of water from the outside, and the amount of water to be introduced was about 20 times the weight of the biomass, so that the saccharide solution concentration obtainable therefrom was low.

On the contrary, in the present invention, as a portion of the biomass solid fraction 20 is immediately liquefied by the enzyme 30 in the enzymatic liquefaction tank 21 which is a pressure vessel, the amount of water required therefor can be suppressed to about 4 times the weight of the biomass, and the saccharide solution concentration can be increased accordingly.

In "Table 1" described below, a comparison is made between the product of the present invention and a conventional product in terms of the relationship between the amounts of the biomass solid fraction and water, and the saccharide concentration. Meanwhile, this Comparative Example is only for illustrative purposes, and since the relationship varies depending on the kind of the biomass raw material, the present invention is not intended to be limited to this.

TABLE 1

| | Example | | |
|---|---|---|---|
| | Solid fraction | Water fraction | Saccharide concentration |
| Product of Invention | 1 { 0.5(Saccharide fraction)<br>0.5(Other than saccharides) | 4 | 10% |
| Conventional product | 1 { 0.5(Saccharide fraction)<br>0.5(Other than saccharides) | 20 | 2.5% |

As indicated in Table 1, in regard to the product of the invention, the amount of the water fraction reaches only ⅕ (4/20) of the conventional product as a result of enzymatic liquefaction, and the saccharide concentration can be adjusted to 10%. This enables to obtain a saccharide solution having a concentration four times higher than the concentration of 2.5% in the case of conventional slurrying. Also, when the amount of water fraction included in the biomass solid fraction 20 is reduced, a more concentrated saccharide solution can be obtained.

As the result, the amount of water that is separated by solid-liquid separation in the saccharification process is also small, and the plant efficiency is increased. Also, reduction to a large extent of the amount of effluent water in the case of subjecting the separated water to a separate effluent treatment can be promoted.

Furthermore, although the enzymatic liquefaction tank 21 is provided with the stirring means 22, the present invention is not intended to be limited to this, and for example, stirring may also be carried out with a circulation means induced by a pump, or the like.

Also, in the present embodiment, the enzymatic liquefaction tank 21 is provided with a pH meter 31.

By providing this pH meter 31, the pH of the liquid in the enzymatic liquefaction tank 21 can be measured, so that liquefaction can be carried out efficiently by adjusting the pH of the liquid in the enzymatic liquefaction tank 21 to the pH at which the enzyme efficiently exhibits a saccharification ability, by adding an acid or an alkali to the enzymatic liquefaction tank 21.

Furthermore, by providing the pH meter 31, the presence of organic acids remaining in the slurry-like biomass solid fraction 24 can be checked.

Thereby, the status of generation of organic acids (for example, acetic acid) produced by hydrothermal decomposition can be monitored.

Furthermore, when the pH of the liquid in the enzymatic liquefaction tank 21 is significantly decreased, it can be considered that organic acids (acetic acid and the like) are generated by hydrothermal decomposition. Thus, it is desirable to perform temperature control of the pressurized hot water of the hydrothermal decomposition unit 17.

Furthermore, the control of the hydrothermal decomposition reaction may also be carried out by measuring the pH with the pH meter 31, and thus controlling the amount of the pressurized hot water supplied.

Other examples of the method for the control of the hydrothermal decomposition unit 17 based on pH include a method of controlling the hydrothermal decomposition reaction by the control (reaction time) of the amount of the biomass raw material 11 supplied; a method of controlling the hydrothermal decomposition reaction by controlling the scraping-up speed (reaction time) of the biomass raw material 11 by the first screw means 14; a method of controlling the hydrothermal decomposition reaction by controlling the liquid level (reaction time) of the gas-liquid interface 13*a* of the apparatus main body 13; and a method of controlling the hydrothermal decomposition reaction by controlling the amount of discharge of the hot water discharge liquid 16 (reaction time).

Here, the biomass supplied to the hydrothermal decomposition unit 17 is not particularly limited, and refers to any living organism, or accumulation of organic materials derived from living organisms, that has been incorporated into the material circulation system of the global biosphere (see JIS K 3600 1258). However, in the present invention, it is preferable to use, in particular, woody cellulose-based resources, for example, hardwood-based cellulose and herbaceous cellulose resources, agricultural wastes, food wastes and the like.

The particle size of the biomass raw material 11 is not particularly limited, but it is preferable to mill the biomass raw material to a size of 5 mm or less.

In the present embodiment, prior to the supply of biomass, the biomass raw material may be pretreated using, for example, a milling apparatus as a pretreatment apparatus. Also, the biomass raw material may be washed with a washing apparatus.

When the biomass raw material 11 is, for example, hull or the like, the raw material may be supplied directly to the biomass supply unit 12 without being treated by milling.

Furthermore, the reaction temperature in the hydrothermal decomposition unit 17 is preferably set to the range of 140° C. to 240° C. Even more preferably, the reaction temperature is set to 180° C. to 230° C.

This is because at a low temperature of below 140° C., the hydrothermal decomposition rate is low, a long decomposition time is needed, and this leads to an increase in the size of the apparatus, which is not preferable. On the other hand, it is because at a temperature of above 240° C., the decomposition rate becomes excessively high, transition of cellulose components from solid to the liquid side is increased, and also, excessive decomposition of hemicellulose-based saccharides is accelerated, which is not preferable.

Furthermore, hemicellulose components dissolve at near about 140° C., cellulose dissolves at near about 230° C., and lignin components dissolve at near 140° C.; thus, it is desirable to set the reaction temperature to the range of 180° C. to 230° C., in which cellulose is left in the solid fraction side, while the hemicellulose components and lignin components have sufficient decomposition rates.

Regarding the reaction pressure, it is preferable to add a pressure of only 0.1 to 0.5 MPa to the saturated vapor pressure of water at the respective temperatures of the reaction temperature of the apparatus main body 13 (180° C. to 240° C.)

Also, the reaction time is preferably set to 20 minutes or less, or to 3 minutes to 10 minutes. This is because if the reaction is carried out too long, the proportion of over-decomposed products is increased, which is not preferable.

Examples of the biomass supply unit 12 that supplies at a pressure ranging from normal pressure to an added pressure include means such as a screw, a piston pump, and a slurry pump.

Also, regarding the hydrothermal decomposition apparatus, a vertical type apparatus is used in the present embodiment; however, the present invention is not intended to be limited to this, and a slanting type hydrothermal decomposition apparatus having a gas-liquid interface 13*a* may also be used.

Here, a slanting type or vertical type hydrothermal decomposition apparatus is used because the gas generated in the hydrothermal decomposition reaction, the gas brought in with the raw material, and the like can escape rapidly from the upper side, which is preferable. Also, since the decomposition product is extracted using pressurized hot water 15, the concentration of the extract increases from the upper side toward the lower side, which is preferable in view of the extraction efficiency.

As discussed above, according to the present embodiment, when a main cellulose component and hemicellulose components from a biomass raw material are subjected to a decomposition treatment in the state of solid-liquid contact, and the biomass solid fraction 20 as a decomposition product thereof is supplied to the inside of the enzymatic liquefaction tank 21 to be enzymatically liquefied, the biomass solid fraction 20 is liquefied, and the liquefaction product becomes a liquid seal. Thus, effluence of a gas for pressurization can be prevented.

Furthermore, since it is not necessary to supply a large amount of water from the outside to convert the biomass solid fraction into slurry, the amount of water introduced at the time of slurrying is reduced. Thus, an increase in the plant efficiency can be promoted.

The present embodiment was explained using a hydrothermal decomposition apparatus as a biomass treatment unit that performs a decomposition treatment of biomass. However, the present invention is not limited to this, and for example, any of an alkali decomposition-treating biomass treatment unit (for example, decomposition based on the utilization of sodium hydroxide, slaked lime, or ammonia) or an acid decomposition-treating biomass treatment unit (decomposition by a dilute sulfuric acid or the like) can be applied to a system in which a gas-liquid interface is provided, and when the biomass solid fraction 20 after the treatment is discharged from the biomass treatment unit in a solid state, the treated biomass solid fraction 20 is converted to slurry by installing an enzymatic saccharification tank 21 to which an enzyme 30 is added, and the slurry is discharged through a discharge mechanism at a pressure ranging from an added pressure to normal pressure.

Second Embodiment

Next, another embodiment of the biomass hydrothermal decomposition system according to the present invention will be described with reference to the drawings. Meanwhile, the same members as the members of the biomass hydrothermal decomposition system of the first embodiment will be assigned with the same reference numerals, and further explanations thereof will not be repeated here.

Figure 4:
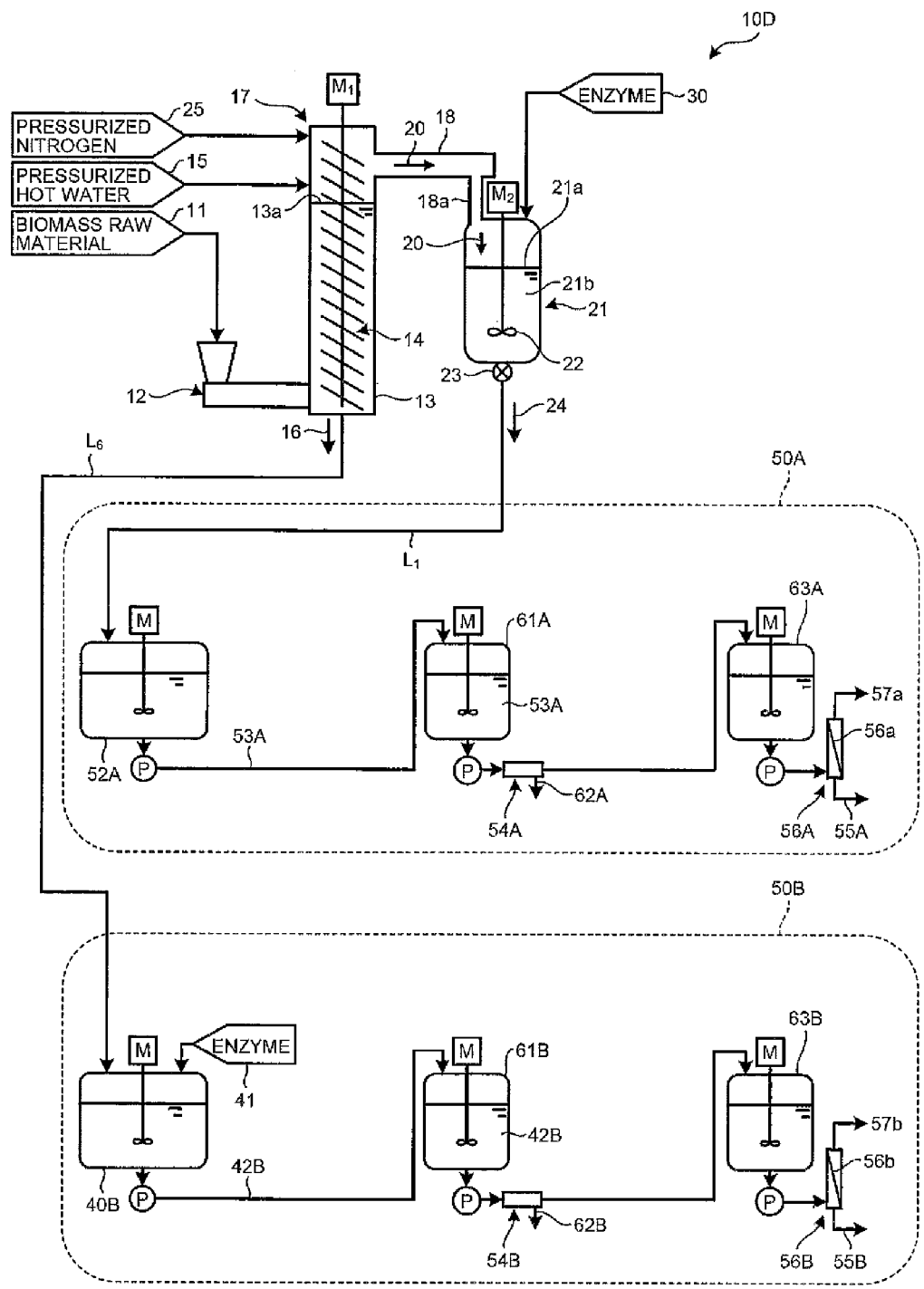
FIG. 4 is an outline diagram of a biomass hydrothermal decomposition system according to a second embodiment.

FIG. 4 is an outline diagram illustrating the biomass hydrothermal decomposition system according to the second embodiment.

As can be seen from FIG. 4, a biomass hydrothermal decomposition system 10D includes, with respect to the biomass hydrothermal decomposition system 10A of the first embodiment: a C6 saccharification/saccharide concentration apparatus 50A that performs enzymatic saccharification of the biomass solid fraction 20 containing mainly cellulose component into hexoses (C6 saccharides) and the like, and concentrates the saccharides; and a C5 saccharification/saccharide concentration apparatus 50B that performs enzymatic saccharification of the hot water discharge liquid 16 containing mainly hemicellulose components into pentoses (C5 saccharides) and the like, and concentrates the saccharides. In FIG. 4, reference numeral M represents a motor that drives a stirring means, and P represents a liquid transporting pump.

These C6 saccharification/saccharide concentration apparatus 50A and C5 saccharification/saccharide concentration apparatus 50B have a first saccharification tank 52A that further subjects the biomass solid fraction 20 that has been liquefied in the enzymatic liquefaction tank 21, to enzymatic saccharification by the enzyme 30, and a second saccharification tank 40B that subjects the hot water discharge liquid 16 from the hydrothermal decomposition unit 17 by an enzyme 41, to enzymatic saccharification; a first solid-liquid separation apparatus 54A and a second solid-liquid separation apparatus 54B that separate solid fractions from a saccharide solutions 53A and 42B after saccharification; and water separation apparatuses 56A and 56B having reverse osmosis (RO) membranes 56a and 56b, in which water 57a and 57b is removed from the saccharide solutions 53A and 42B separated from the first solid-liquid separation apparatus 54A and the second solid-liquid separation apparatus 54B, and concentrated saccharide solutions 55A and 55B are obtained.

The first solid-liquid separation apparatus 54A and the second solid-liquid separation apparatus 54B can use, for example, a screw decanter, a sand filtering apparatus, an MF membrane and the like, singly or in combination, and thereby the solid-liquid separation apparatuses remove solid materials and promote protection of the RO membranes 56a and 56b. Furthermore, by using an ultrafiltration membrane (UF membrane) in the upstream side of the RO membranes 56a and 56b, protection of the RO membranes 56a and 56b can be promoted, and also, recovery of the enzyme is enabled. Thus, the enzyme can be recycled.

Furthermore, loose RO membranes, nanofiltration membranes (NF membranes) and the like may also be used for the water separation apparatuses 56A and 56B.

In the present embodiment, the enzyme 30 is used such that a required amount of enzyme is added to the enzymatic liquefaction tank 21. Therefore, no enzyme is added to the first saccharification tank 52A that performs enzymatic saccharification at normal pressure; however, the present invention is not limited to this.

Figure 5:
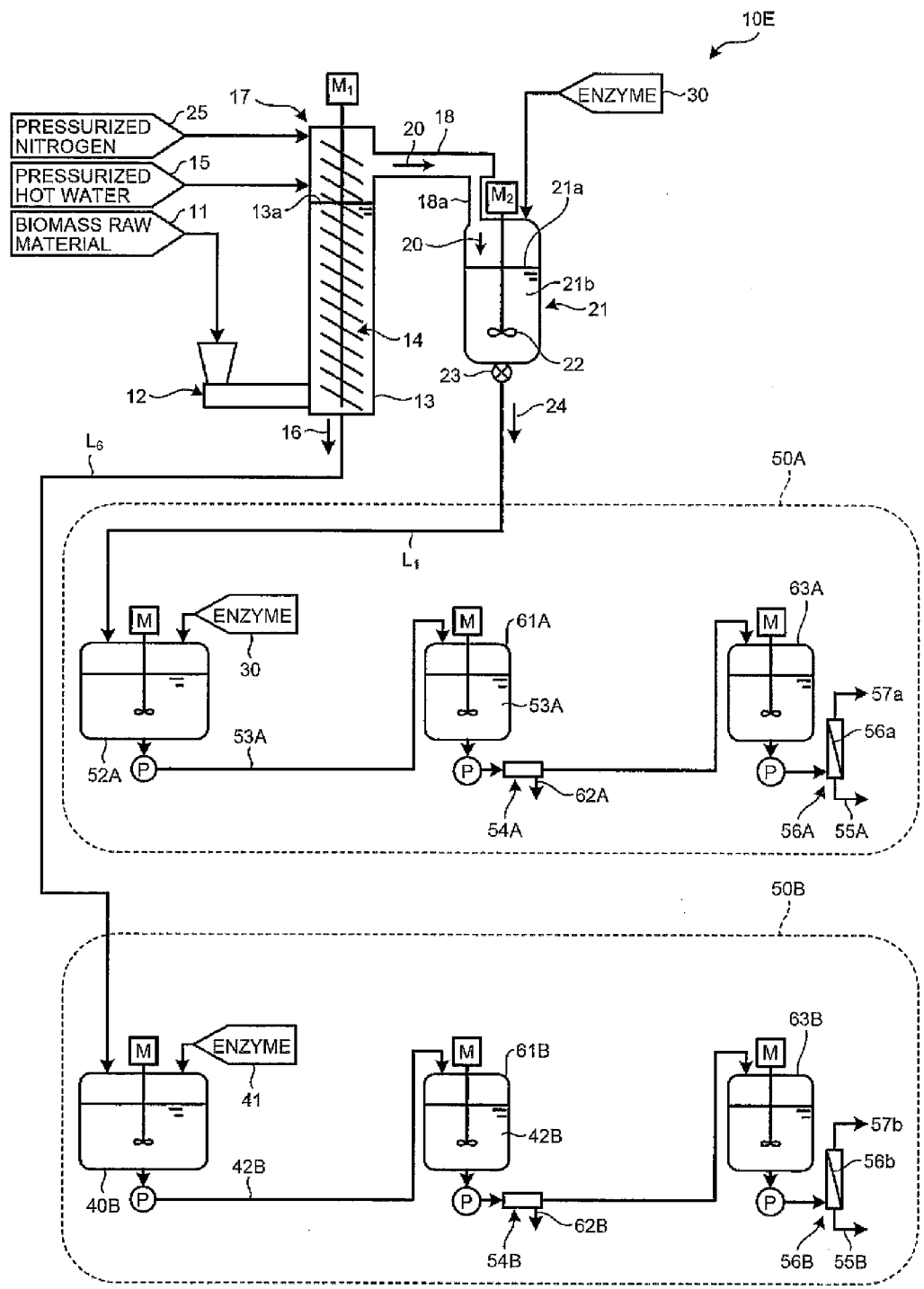
FIG. 5 is an outline diagram of another biomass hydrothermal decomposition system according to the second embodiment.

For example, as shown in another biomass hydrothermal decomposition system 10E according to the second embodiment illustrated in FIG. 5, the enzyme 30 may be added to the first saccharification tank 52A, and monosaccharification may be promoted under normal pressure conditions.

On the contrary, in the biomass hydrothermal decomposition system 10D according to the second embodiment illustrated in FIG. 4, since the addition of the enzyme 30 can be carried out at one site, the apparatus configuration is simpler than that of the system of FIG. 5.

Next, the order of the treatment processes of these C6 saccharification/saccharide concentration apparatus 50A and C5 saccharification/saccharide concentration apparatus 50B will be explained.

<Enzymatic Saccharification Process>

First, in the first saccharification tank 52A, the liquefied biomass solid fraction 24 containing a portion of low molecular weight oligomers is introduced through a discharge line $L_1$, the enzyme 30 is further added thereto, and saccharification occurs as a result of the enzymatic reaction for the enzymatic saccharification process.

On the other hand, in the second saccharification tank 40B, the hot water discharge liquid 16 is introduced through a hot water discharge liquid supply line $L_6$, the enzyme 41 is added thereto, and saccharification occurs as a result of the enzymatic reaction for the enzymatic saccharification process.

Meanwhile, since the following processes are the same in the solid-liquid separation treatment process for C6 saccharides and C5 saccharides, the treatment process of the C6 saccharification/saccharide concentration apparatus 50A will be explained.

<Solid-Liquid Separation Process>

Next, the saccharide solution 53A is stored in a first saccharide solution tank 61A, and subsequently, a solid residual liquid 62A such as lignin is separated by the first solid-liquid separation apparatus 54A. Thereafter, the saccharide solution 53A is stored in a second saccharide solution tank 63A.

<Saccharide Concentration Process>

Next, the saccharide solution 53A is treated by removing water 57A therefrom by the water separation apparatus 56A including the RO membrane 56a, and thus a concentrated saccharide solution 55A is obtained.

This concentrated saccharide solution 55A serves as various organic raw materials in the fermentation treatment of subsequent processes that are not shown in the diagram.

Since the biomass solid fraction 24 that has been enzymatically liquefied is in a slurry form, stirring, transport and the like can be carried out with favorable operability.

Furthermore, concentration of saccharides can be carried out efficiently by a membrane treatment using various membranes.

Also, since the separated solid residual liquid 62A (62B) such as lignin is highly caloric, the solid residual liquid can be used for fuel applications. Also, the solid residual liquid 62A (62B) such as lignin, can be utilized in organic fertilizer applications or in chemical raw material applications (utilization thereof as an adhesive for lignin, and the like).

As such, the method for producing a saccharide solution using a biomass raw material of the present invention can efficiently produce a saccharide solution from a biomass raw material by, as illustrated in FIGS. 4 and 5, supplying a biomass raw material 11 containing cellulose, hemicelluloses and lignin at a pressure ranging from normal pressure to an added pressure, hydrothermally decomposing the biomass raw material 11 by a hydrothermal decomposition unit 17 using pressurized hot water 15, dissolving lignin components and hemicellulose components in the pressurized hot water 15, subsequently feeding a biomass solid fraction 20 discharged from the hydrothermal decomposition unit 17 and an enzyme 30 into an enzymatic liquefaction tank 21 that is in connection with the hydrothermal decomposition unit 17, obtaining a slurry-like biomass solid fraction 24 in which a portion of the biomass solid fraction is liquefied by the enzyme, enzymatically saccharifying the slurry-like biomass solid fraction 24 to obtain a saccharide solution 53A, subsequently separating a solid fraction, and then removing water.

Third Embodiment

Next, another embodiment of the biomass hydrothermal decomposition system according to the present invention will be explained with reference to the drawings. Meanwhile, the same members as the members of the biomass hydrothermal decomposition systems of the first to third embodiments will be assigned with the same reference numerals, and further explanations thereof will not be repeated here.

Figure 6:
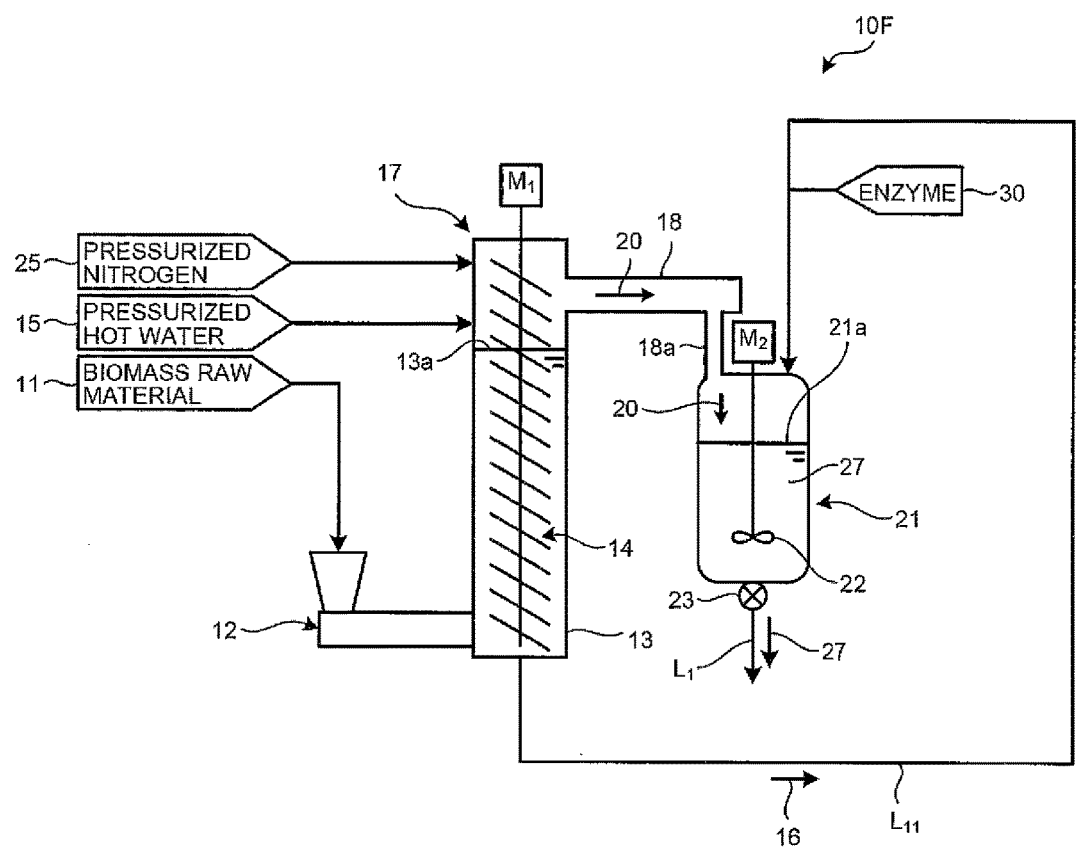
FIG. 6 is an outline diagram of a biomass hydrothermal decomposition system according to a third embodiment.

FIG. 6 is an outline diagram illustrating the biomass hydrothermal decomposition system according to the third embodiment.

Figure 7:
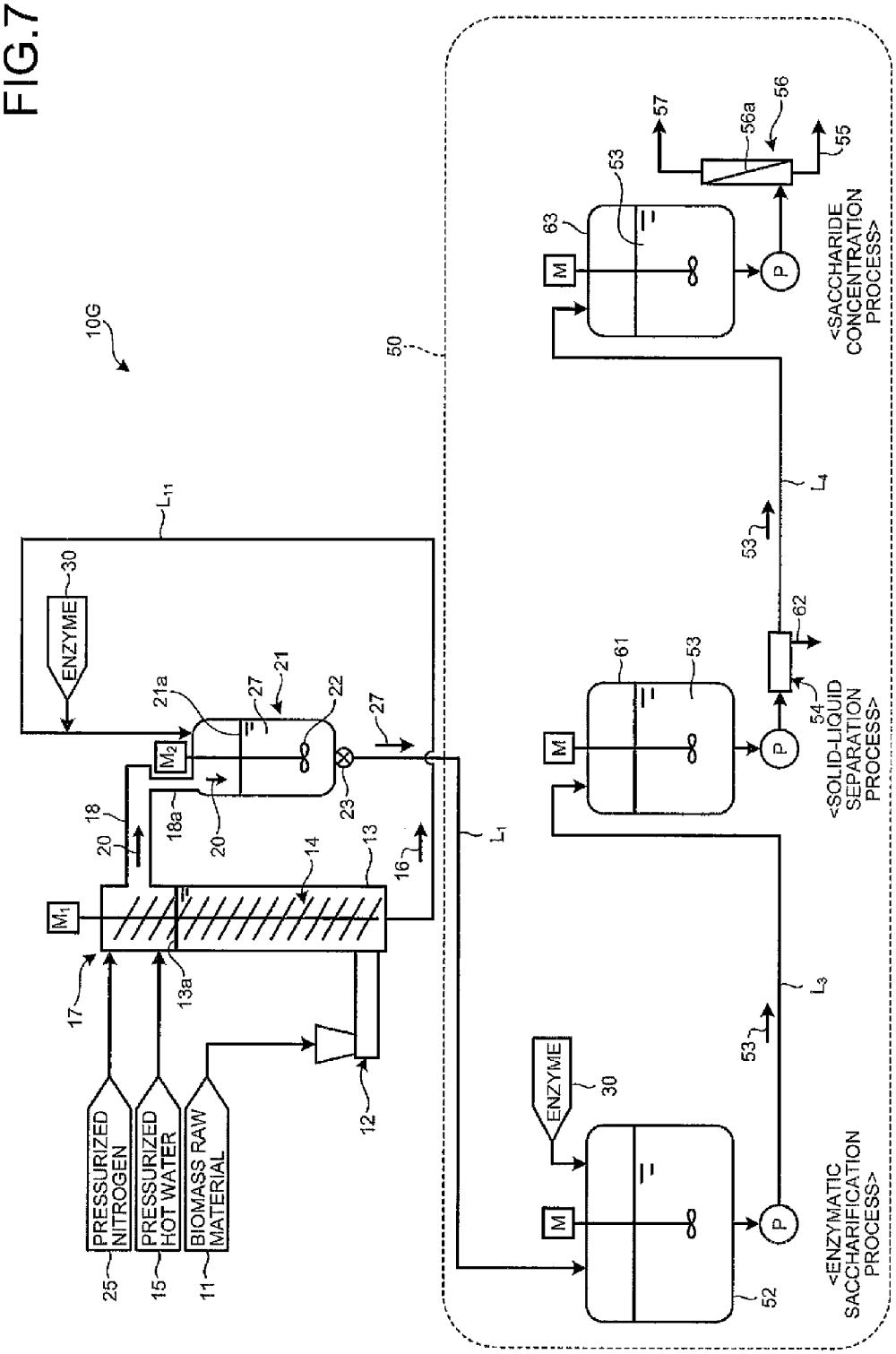
FIG. 7 is an outline diagram of another biomass hydrothermal decomposition system according to the third embodiment.

FIG. 7 is an outline diagram illustrating another biomass hydrothermal decomposition system according to the third embodiment.

As illustrated in FIG. 6, a biomass hydrothermal decomposition system 10F includes, with respect to the biomass hydrothermal decomposition system 10A of the first embodiment, a hot water discharge liquid inlet line $L_{11}$ that introduces the hot water discharge liquid 16 containing a biomass hot water-soluble fraction discharged from the hydrothermal decomposition unit 17, into the enzymatic liquefaction tank 21 to which the enzyme 30 is added.

According to the present embodiment, the saccharification/saccharide concentration apparatus 50B illustrated in FIG. 4 and FIG. 5 explained in the second embodiment is not needed, and the apparatus configuration can be simplified.

In order to suppress excessive decomposition of hemicelluloses (decomposition initiation temperature: about 140° C. to 180° C.) that are contained in the water fraction included in the biomass solid fraction 20, the temperature of the hot water discharge liquid 16 introduced is optionally lowered by a cooling means that is not shown in the diagram, in accordance with the temperature of the biomass solid fraction 20 or the capacity of the enzymatic liquefaction tank 21, and may be appropriately set so that the liquid temperature of the enzymatic liquefaction tank 21 is cooled to 140° C. or lower.

Furthermore, the cooling means 26 provided in the enzymatic liquefaction tank 21 of the aforementioned biomass hydrothermal decomposition system 10B as illustrated in FIG. 2 may also be installed in the present embodiment.

In the present embodiment, the biomass solid fraction 20, which is a hot water-insoluble fraction that serves as a hexose raw material, is dropped into the discharge liquid 16 containing a biomass hot water-soluble fraction that serves as a pentose raw material, and thus a slurry-like mixed liquefaction product 27 is obtained. Thereby, the saccharification process can be carried out in a single line.

Next, a saccharification/saccharide concentration apparatus 50 that performs enzymatic saccharification using the mixed liquefaction product 27 and concentrates saccharides will be explained using FIG. 7.

FIG. 7 is an outline diagram illustrating a biomass hydrothermal decomposition system 10G according to the third embodiment.

As illustrated in FIG. 7, the biomass hydrothermal decomposition system 10G is a biomass hydrothermal decomposition system further including a saccharification/saccharide concentration apparatus 50 with respect to the biomass hydrothermal decomposition system 10F. This saccharification/saccharide concentration apparatus 50 includes a saccharification tank 52 that further subjects the mixed liquefaction product 27 having a portion thereof saccharified by the enzyme 30, to enzymatic saccharification by the enzyme 30; a solid-liquid separation apparatus 54 that separates a solid fraction from a saccharide solution 53 obtained after saccharification; and a water separation apparatus 56 having a reverse osmosis (RO) membrane 56a, in which water 57 is removed from the saccharide solution 53 separated in the solid-liquid separation apparatus 54, and a concentrated saccharide solution 55 is obtained.

The solid-liquid separation apparatus 54 can use, for example, a screw decanter, a sand filtering apparatus and an MF membrane, singly or in combination, and thereby removes solid materials and promotes protection of the RO membrane 56a. Furthermore, by using an ultrafiltration membrane (UF membrane) in the upstream side of the RO membrane 56a, protection of the RO membrane can be promoted, and also, recovery of the enzyme is enabled. Thus, the enzyme can be recycled.

Furthermore, a loose RO membrane, a nanofiltration membrane (NF membrane), and the like may also be used in the water separation apparatus 56.

Next, the order of the treatment processes of this saccharification/saccharide concentration apparatus 50 will be explained.

The mixed liquefaction product 27 is a mixture of the biomass solid fraction 20 which is a hot water-insoluble fraction that serves as a hexose raw material, and a discharge liquid 16 including a biomass hot water-soluble fraction that serves as a pentose raw material. Therefore, C6 saccharification and C5 saccharification proceed in the same line.

<Enzymatic Saccharification Process>

First, in the saccharification tank 52, the mixed liquefaction product 27 having a portion thereof saccharified by the enzyme 30 is introduced through the discharge line $L_1$, the enzyme 30 is further added thereto, and saccharification occurs as a result of the enzymatic reaction for the enzymatic saccharification process.

Meanwhile, it is not necessary to add the enzyme 30 to the saccharification tank 52, if the enzyme is added in a required amount to the enzymatic liquefaction tank 21.

<Solid-Liquid Separation Process>

Next, the saccharide solution 53 is stored in a first saccharide solution tank 61, and subsequently, a solid residual liquid 62 such as lignin, is separated by the solid-liquid separation apparatus 54. Thereafter, the saccharide solution 53 is stored in a second saccharide solution tank 63. In the drawing, reference numerals $L_3$ and $L_4$ represent saccharide solution supply lines that supply the saccharide solution 53.

<Saccharide Concentration Process>

Next, the saccharide solution 53 is treated by removing water 57 therefrom by a water separation apparatus 56 including an RO membrane 56a, and thus a concentrated saccharide solution 55 is obtained.

This concentrated saccharide solution 55 serves as various organic raw materials for the fermentation treatment of subsequent processes that are not shown in the diagram.

In the present embodiment, since saccharification is achieved using the mixed liquefaction product 27, saccharification is achieved at a low substrate concentration, and saccharification is enabled in a short reaction time.

Furthermore, since the mixed liquefaction product is in a slurry form, stirring, transport and the like can be carried out with favorable operability.

Also, since saccharification is achieved at a low substrate concentration, reduction of the amount of enzyme used can be promoted.

Furthermore, concentration of saccharides can be carried out efficiently by a membrane treatment using various membranes.

Also, the separated solid residual liquid 62 such as lignin is highly caloric, the solid residual liquid can be used for fuel applications. Also, the solid residual liquid 62 such as lignin, can be utilized in organic fertilizer applications or in chemical raw material applications (utilization thereof as an adhesive of lignin, and the like).

As such, the method for producing a saccharide solution using a biomass raw material of the present invention can efficiently produce a saccharide solution 53 from a biomass raw material 11 by, as illustrated in FIG. 7, supplying a biomass raw material 11 containing cellulose, hemicelluloses and lignin at a pressure ranging from normal pressure to an added pressure, hydrothermally decomposing the biomass raw material 11 by a hydrothermal decomposition unit 17 using pressurized hot water 15, dissolving lignin components and hemicellulose components in the pressurized hot water 15, subsequently feeding the biomass solid fraction 20 discharged from the hydrothermal decomposition unit 17 into an enzymatic liquefaction tank 21 that is in connection with the hydrothermal decomposition unit 17 and has an enzyme 30 and a discharge liquid 16 introduced therein, obtaining a mixed liquefaction product 27 in which a portion of the biomass solid fraction is liquefied by the enzyme 30, discharging this mixed liquefaction product 27 from a pressurized state to a normal pressure state, completing enzymatic saccharification in the saccharification tank 52 to obtain a saccharide solution 53, subsequently separating a solid fraction, and then removing water therefrom.

In the present embodiment, since the discharge liquid 16 is used at the time of slurrying in the enzymatic liquefaction tank 21, and introduction of water from the outside may be deleted, the saccharification concentration can be increased up to, for example, 1.5 wt % to 8 wt %. As the result, the saccharide solution concentration apparatus to be installed in the downstream side may be unnecessary, or compaction of the saccharide solution concentration apparatus can be promoted.

As such, according to the present embodiment, when a main cellulose component and hemicellulose components from a biomass raw material are subjected to a decomposition treatment in the state of solid-liquid contact, and the biomass solid fraction 20 as a decomposition product thereof is fed into the liquid that has been introduced into an enzymatic liquefaction tank 21, the biomass solid fraction 20 is converted to slurry, and the slurry becomes a liquid seal. Thus, effluence of a gas for pressurization can be prevented. Thereby, effluence of the gas for pressurization (for example, pressurized nitrogen or pressurized air) is prevented, and reduction to a large extent of the running cost can be promoted.

At this time, since the discharge liquid 16 discharged from the hydrothermal decomposition unit 17 is introduced into the enzymatic liquefaction tank 21, it is unnecessary to form slurry using water from the outside.

Furthermore, since the enzyme 30 is introduced into the enzymatic liquefaction tank 21, partially saccharify in a pressurized state, and also, a partially saccharified mixed liquefaction product 27 is discharged at a pressure ranging from a pressurized state to a normal pressure state, and saccharification is achieved in the saccharification tank 52 in a normal pressure state, the efficiency of the saccharification treatment is enhanced.

Thus, according to the present embodiment, when the hot water discharge liquid 16 is used without supplying water from the outside at the time of slurrying, and also, enzymatic liquefaction is carried out using the enzyme 30, reduction to a large extent of the amount of water consumed in the whole plant is enabled, and reduction in cost can be promoted.

Furthermore, since saccharification is achieved using a mixed liquefaction product 27 obtained by mixing a slurry-like biomass solid fraction 20 that serves as a hexose raw material, and a hot water discharge liquid 16 that serves as a pentose raw material, an increase in the absolute amount of saccharides recovered from a single enzymatic saccharification tank 21 can be promoted.

Furthermore, since saccharification is achieved using a mixed liquefaction product 27 obtained by mixing a slurry-like biomass solid fraction 20 that serves as a hexose raw material and a hot water discharge liquid 16 that serves as a pentose raw material, miscibility of the enzyme and the biomass is improved. Therefore, the enzyme works more efficiently, the amount of enzyme consumed in the saccharification can be reduced, and as a result, reduction of the cost for enzyme use can be promoted.

Furthermore, since saccharification is achieved using a mixed liquefaction product 27 obtained by mixing a slurry-like biomass solid fraction 20 that serves as a hexose raw material, and a hot water discharge liquid 16 that serves as a pentose raw material, the saccharification line cannot be made into a dual system such as a conventional line, and can be made into a single line of a single system. Therefore, the enzymatic saccharification process is simplified, and reduction of the facility cost and the running cost can be promoted.

Furthermore, since the amount of water consumed can be reduced, the amount of waste water generated can be reduced, and reduction of the waste water treatment cost can be promoted.

Fourth Embodiment

Next, another embodiment of the biomass hydrothermal decomposition system according to the present invention will be explained with reference to the drawings. Meanwhile, the same members as the members of the biomass hydrothermal decomposition system of the third embodiment will be assigned with the same reference numerals, and further explanations thereof will not be repeated here.

Figure 8:
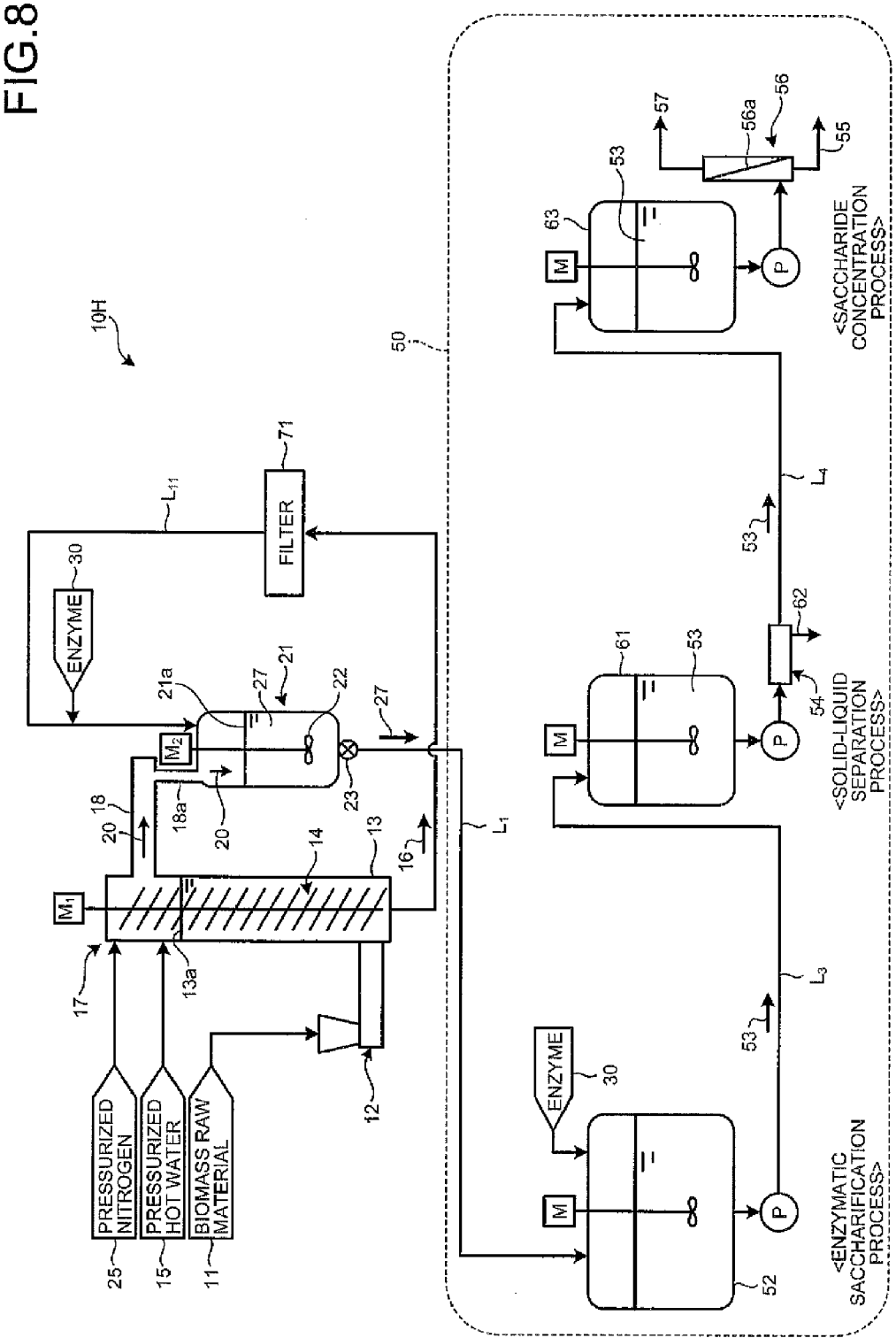
FIG. 8 is an outline diagram of a biomass hydrothermal decomposition system according to a fourth embodiment.

FIG. 8 is an outline diagram illustrating the biomass hydrothermal decomposition system according to the fourth embodiment.

As illustrated in FIG. 8, a biomass hydrothermal decomposition system 10H is provided with a filter 71 in the hot water discharge liquid inlet line $L_{11}$ with respect to the biomass hydrothermal decomposition system 10G of the third embodiment. By installing this filter 71, a solid fraction such as lignin in the hot water discharge liquid 16 is separated. Thereby, inhibition of saccharification by lignin can be prevented.

Fifth Embodiment

Next, another embodiment of the biomass hydrothermal decomposition system according to the present invention will be explained with reference to the drawings. Meanwhile, the same members as the members of the biomass hydrothermal decomposition system of the third embodiment will be assigned with the same reference numerals, and further explanations thereof will not be repeated here.

Figure 9:
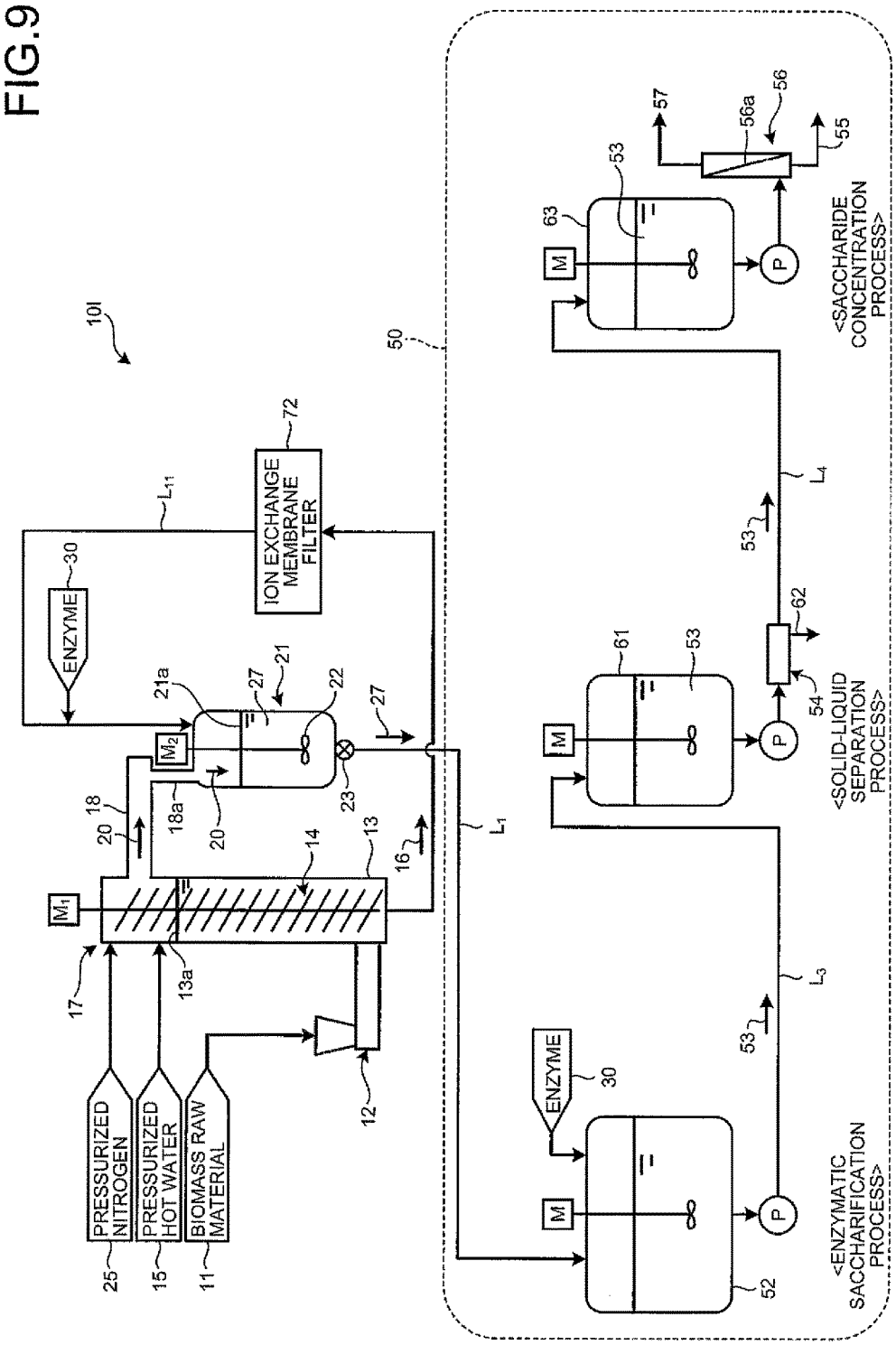
FIG. 9 is an outline diagram of a biomass hydrothermal decomposition system according to a fifth embodiment.

FIG. 9 is an outline diagram illustrating the biomass hydrothermal decomposition system according to the fifth embodiment.

As illustrated in FIG. 9, a biomass hydrothermal decomposition system 10I is provided with an ion exchange membrane filter 72 in the hot water discharge liquid inlet line $L_{11}$ with respect to the biomass hydrothermal decomposition system 10G of the third embodiment. By installing this ion exchange membrane filter 72, acidic materials solubilized in the hot water discharge liquid 16 are removed by ion exchange. Thereby, inhibition of saccharification by acidic materials is prevented.

Sixth Embodiment

Next, another embodiment of the biomass hydrothermal decomposition system according to the present invention will be explained with reference to the drawings. Meanwhile, the same members as the members of the biomass hydrothermal decomposition system of the third embodiment will be assigned with the same reference numerals, and further explanations thereof will not be repeated here.

Figure 10:
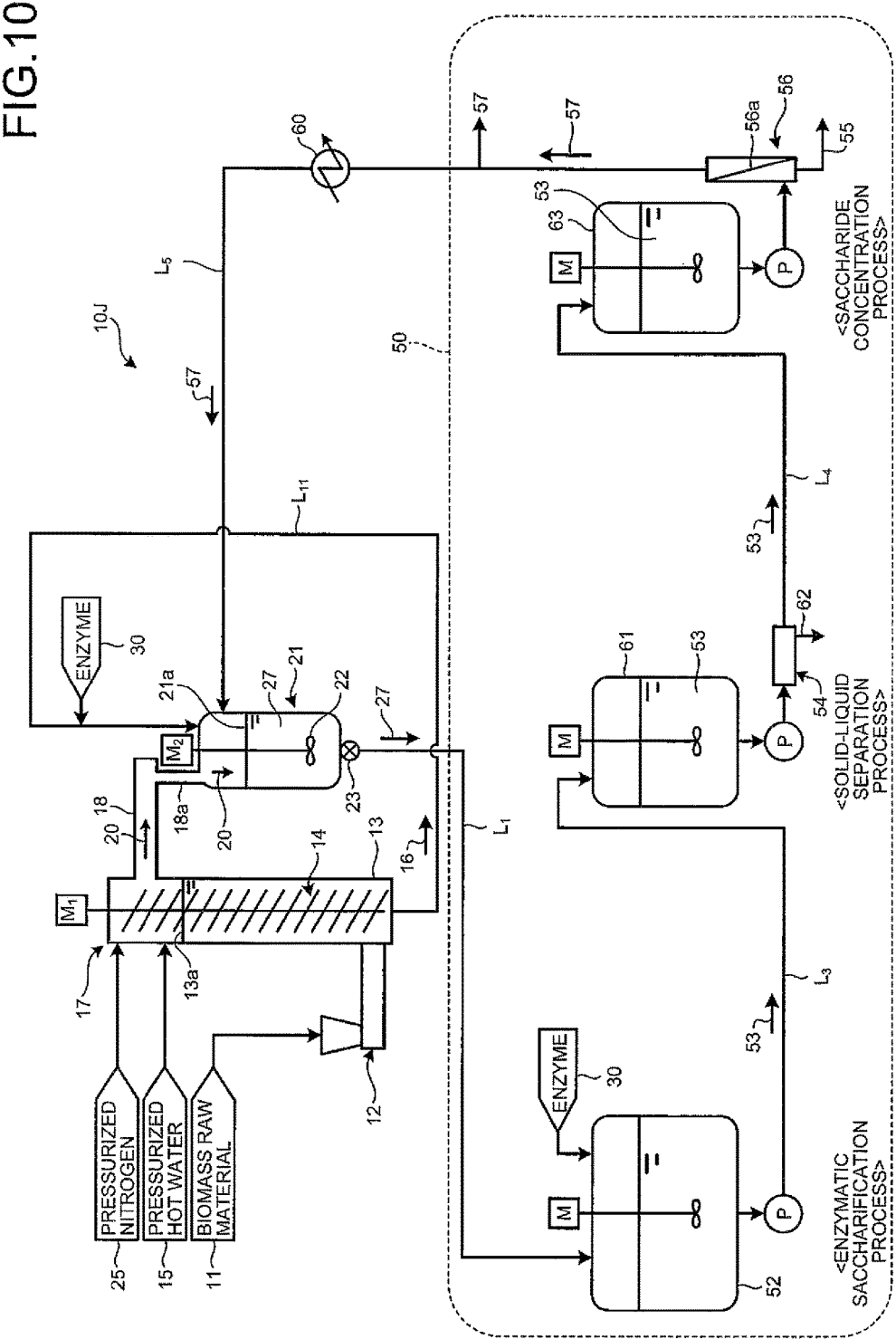
FIG. 10 is an outline diagram of a biomass hydrothermal decomposition system according to a sixth embodiment.

FIG. 10 is an outline diagram illustrating the biomass hydrothermal decomposition system according to the sixth embodiment.

As illustrated in FIG. 10, a biomass hydrothermal decomposition system 10J includes a water return line $L_5$ that further returns water 57 that has been separated from the water separation apparatus 56 to the enzymatic liquefaction tank 21, with respect to the biomass hydrothermal decomposition system 10G of the third embodiment.

Furthermore, this water return line $L_5$ has a cooler 60 interposed therein so that water 57 is cooled to a predetermined temperature and then is returned to the enzymatic liquefaction tank 21.

Thereby, the separated water 57 can be recycled.

Seventh Embodiment

Next, another embodiment of the biomass hydrothermal decomposition system according to the present invention will be explained with reference to the drawings. Meanwhile, the same members as the members of the biomass hydrothermal decomposition system of the first embodiment will be assigned with the same reference numerals, and further explanations thereof will not be repeated here.

Figure 11:
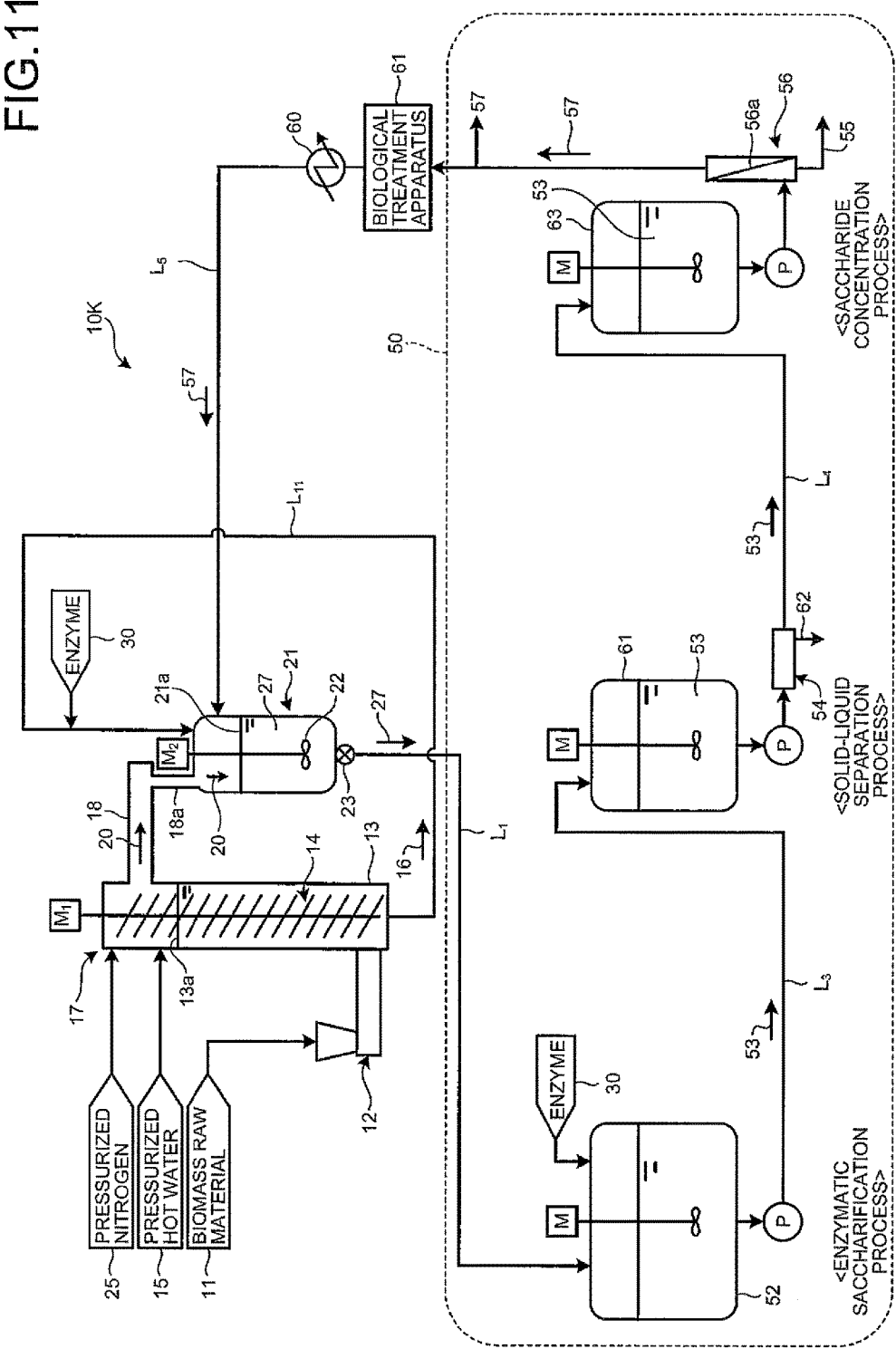
FIG. 11 is an outline diagram of a biomass hydrothermal decomposition system according to a seventh embodiment.

FIG. 11 is an outline diagram illustrating the biomass hydrothermal decomposition system according to the seventh embodiment.

As illustrated in FIG. 11, a biomass hydrothermal decomposition system 10K is further provided with a biological treatment apparatus 61 in the water return line $L_5$ with respect to the biomass hydrothermal decomposition system 10J of the sixth embodiment, so that water 57 is biologically treated and then is returned to the enzymatic liquefaction tank 21.

Since the water 57 separated by the RO membrane 56a in the saccharide concentration process contains reaction inhibiting materials (low molecular weight organic compounds), treatment can be carried out easily by a biological treatment apparatus 61. Also, methane can be recovered and utilized in fuel and the like by using, for example, a methane fermentation biological treatment apparatus as the biological treatment apparatus 61.

As discussed above, when the biomass hydrothermal decomposition system according to the present invention is used, a biomass solid fraction 20 is enzymatically saccharified, and handling thereof is made easier. Also, the biomass solid fraction becomes appropriate for the subsequent saccharification process, and efficient production of a saccharide solution (C6 saccharides and C5 saccharides) can be carried out. Furthermore, by using this saccharide solution as a starting point, for example, various organic raw materials (for example, alcohols, petroleum substitutes, and amino acids) for LPG, car fuels, jet fuels for airplanes, kerosene, diesel oil, various heavy oils, fuel gas, naphtha, ethylene glycol which is a naphtha cracking product, lactic acid, alcohols (ethanol and the like), amines, alcohol ethoxylate, vinyl chloride polymers, alkylaluminum, PVA, vinyl acetate emulsion, polystyrene, polyethylene, polypropylene, polycarbonate, MMA resin, nylon, and polyester can be efficiently produced. Therefore, substitutes of chemical products derived from petroleum, which is an exhaustible fuel, and a biomass-derived saccharide solution as a production raw material for substitutes thereof can be efficiently utilized.

Furthermore, since a biomass solid fraction is introduced into a liquid, the reaction termination can be carried out highly efficiently by cooling the biomass solid fraction by direct heat exchange with the liquid. Thus, excessive decomposition of residual hemicelluloses, residual lignin, and cellulose as a main component by hot water that are included in the biomass solid fraction, is suppressed. As the result, suppression of the production of reaction inhibiting components is promoted, and also, an increase in the recovery ratio of the cellulose fraction can be promoted.

REFERENCE SIGNS LIST 10A to 10K BIOMASS HYDROTHERMAL DECOMPOSITION SYSTEMS
11 BIOMASS RAW MATERIAL
12 BIOMASS SUPPLY UNIT
13 APPARATUS MAIN BODY
14 FIRST SCREW MEANS
15 PRESSURIZED HOT WATER
16 HOT WATER DISCHARGE LIQUID
17 HYDROTHERMAL DECOMPOSITION UNIT

18 BIOMASS SOLID FRACTION DISCHARGE UNIT
20 BIOMASS SOLID FRACTION
21 ENZYMATIC LIQUEFACTION TANK
22 STIRRING MEANS
23 DISCHARGE UNIT
24 LIQUEFIED BIOMASS SOLID FRACTION
25 PRESSURIZED NITROGEN
27 MIXED LIQUEFACTION PRODUCT
30 ENZYME

The invention claimed is:

1. A saccharide solution production system using a biomass raw material, comprising:
   a biomass supply unit that supplies a biomass raw material containing cellulose, hemicelluloses, and lignin at a pressure ranging from normal pressure to an added pressure;
   a hydrothermal decomposition unit that hydrothermally decomposes the biomass raw material by pressurized hot water, and dissolves lignin components and hemicellulose components in the pressurized hot water;
   a biomass solid fraction discharge unit that is connected to the hydrothermal decomposition unit and discharges a biomass solid fraction from the hydrothermal decomposition unit;
   a pressure vessel including an enzyme supplier and a discharge unit provided in a vicinity of a bottom thereof which is in connection with the biomass solid fraction discharge unit from which the discharged biomass solid fraction is introduced therein, liquefies the biomass solid fraction into biomass slurry containing low molecular weight oligomers with an enzyme supplied from the enzyme supplier under pressurized conditions and discharges the biomass slurry via the discharged unit under pressurized conditions to normal pressure conditions; and
   a first saccharification tank that saccharifies the biomass slurry under normal pressure conditions to obtain a first saccharide solution.

2. The saccharide solution production system using the biomass raw material system according to claim 1, wherein the hydrothermal decomposition unit conveys the biomass raw material that has been supplied from the side of an end of the apparatus main body to the side of the other end of the apparatus main body by a conveyance means inside the apparatus main body, supplies pressurized hot water from the side of an end different from the supply site of the biomass raw material to the inside of the apparatus main body, hydrothermally decomposes the biomass raw material by bringing the biomass raw material and the pressurized hot water into countercurrent contact, transfers hot water-soluble components in a hot water discharge liquid, which is pressurized hot water to be discharged, and separates lignin components and hemicellulose components from the biomass raw material.

3. The saccharide solution production system using the biomass raw material system according to claim 1, further comprising a second saccharification tank that saccharifies a hot water discharge liquid discharged from the hydrothermal decomposition unit to obtain a second saccharide solution.

4. The saccharide solution production system using the biomass raw material system according to claim 1, further comprising:
   a first solid-liquid separation apparatus that separates a solid residue remained in the first saccharide solution obtained after saccharification in the first saccharification tank; and
   a first water separation apparatus that removes water from the first saccharide solution obtained after solid separation.

5. The saccharide solution production system using the biomass raw material system according to claim 3, further comprising:
   a second solid-liquid separation apparatus that separates a solid residue remained in the second saccharide solution obtained after saccharification in the second saccharification tank; and
   a second water separation apparatus that removes water from the second saccharide solution obtained after solid separation.

6. The saccharide solution production system using the biomass raw material system according to claim 1,
   further comprising a hot water discharge liquid inlet line that introduces a hot water discharge liquid including a biomass hot water-soluble fraction, which is discharged from the hydrothermal decomposition unit, to the pressure vessel, by which the biomass slurry is mixed with a hot water discharge liquid to obtain a mixed liquefaction product therein, and the mixed liquefaction product is saccharified in the first saccharification tank to obtain the first saccharide solution and the second saccharide solution.

7. The saccharide solution production system using the biomass raw material system according to claim 6, wherein a filter is interposed in the hot water discharge liquid inlet line.

8. The saccharide solution production system using the biomass raw material system according to claim 6, wherein a cooling means is interposed in the discharge liquid inlet line.

* * * * *